(12) United States Patent  (10) Patent No.: US 8,535,352 B2
Altarac et al. (45) Date of Patent: Sep. 17, 2013

(54) MULTI-LEVEL MINIMALLY INVASIVE SPINAL STABILIZATION SYSTEM

(75) Inventors: Moti Altarac, Irvine, CA (US); Joey Camia Reglos, Lake Forest, CA (US); Stanley Kyle Hayes, Mission Viejo, CA (US)

(73) Assignee: Exactech, Inc., Gainesville, FL (US)

( * ) Notice: Subject to any disclaimer, the term of this patent is extended or adjusted under 35 U.S.C. 154(b) by 1243 days.

(21) Appl. No.: 12/079,676

(22) Filed: Mar. 28, 2008

(65) Prior Publication Data

US 2008/0183215 A1  Jul. 31, 2008

Related U.S. Application Data

(63) Continuation-in-part of application No. 11/726,093, filed on Mar. 20, 2007, and a continuation-in-part of application No. 11/586,849, filed on Oct. 25, 2006, which is a continuation-in-part of application No. 11/362,366, filed on Feb. 23, 2006, application No. 12/079,676, which is a continuation-in-part of application No. 11/427,738, filed on Jun. 29, 2006, now Pat. No. 7,935,134, which is a continuation-in-part of application No. 11/436,407, filed on May 17, 2006, which is a continuation-in-part of application No. 11/033,452, filed on Jan. 10, 2005, which is a continuation-in-part of application No. 11/006,495, filed on Dec. 6, 2004, which is a continuation-in-part of application No. 10/970,366, filed on Oct. 20, 2004.

(60) Provisional application No. 60/920,872, filed on Mar. 30, 2007, provisional application No. 60/701,660, filed on Jul. 22, 2005.

(51) Int. Cl.
*A61B 17/70* (2006.01)

(52) U.S. Cl.
USPC ............ 606/265; 606/260; 606/266; 606/267

(58) Field of Classification Search
USPC ......... 606/246, 253, 254, 256–261, 265–270, 606/278
See application file for complete search history.

(56) References Cited

U.S. PATENT DOCUMENTS 5,443,467 A   8/1995   Biedermann
5,720,751 A   2/1998   Jackson
(Continued)

*Primary Examiner* — Jerry Cumberledge
(74) *Attorney, Agent, or Firm* — Meyertons, Hood, Kivlin, Kowert & Goetzel, P.C.; Eric B. Meyertons

(57) ABSTRACT

A spinal alignment system for interconnecting vertebral bodies is disclosed. The system includes a bone screw polyaxially connected to a seat. The seat includes a top opening, a first rod receiving portion and a second rod receiving portion, a first rod channel and a second rod channel. The system is implanted into a first vertebral body. A first rod is introduced to the seat through the top opening in a first orientation and connected to the first rod receiving portion. A second rod is introduced to the seat through the top opening in a first orientation and connected to the second rod receiving portion. The first and second rods are each moved into a second orientation such that the rods project through the first and second rod channels, respectively. The rods are capable of polyaxial movement with respect to the seat for landing the opposite ends of the rods in adjacent seats of screw systems implanted in other vertebral bodies. A closure mechanism that is configured to lock the polyaxial motion of the rods with respect to the seat and to lock the polyaxial motion of the bone screw with respect to the seat simultaneously or independently is provided. The seat is connectable to a cannula for delivering the first and second rods into the first seat in a percutaneous, minimally invasive procedure.

22 Claims, 27 Drawing Sheets

(56) References Cited

U.S. PATENT DOCUMENTS

| | | | |
|---|---|---|---|
| 6,379,354 B1* | 4/2002 | Rogozinski | 606/260 |
| 7,618,442 B2* | 11/2009 | Spitler et al. | 606/266 |
| 7,686,833 B1* | 3/2010 | Muhanna et al. | 606/257 |
| 7,806,913 B2* | 10/2010 | Fanger et al. | 606/260 |
| 2004/0039384 A1 | 2/2004 | Boehm | |
| 2004/0111088 A1* | 6/2004 | Picetti et al. | 606/61 |
| 2004/0143265 A1 | 7/2004 | Landry | |
| 2004/0260287 A1* | 12/2004 | Ferree | 606/61 |
| 2005/0187548 A1 | 8/2005 | Butler | |
| 2006/0064090 A1* | 3/2006 | Park | 606/61 |
| 2006/0106380 A1 | 5/2006 | Colleran | |
| 2007/0043359 A1 | 2/2007 | Altarac | |
| 2008/0071275 A1* | 3/2008 | Ferree | 606/61 |

* cited by examiner

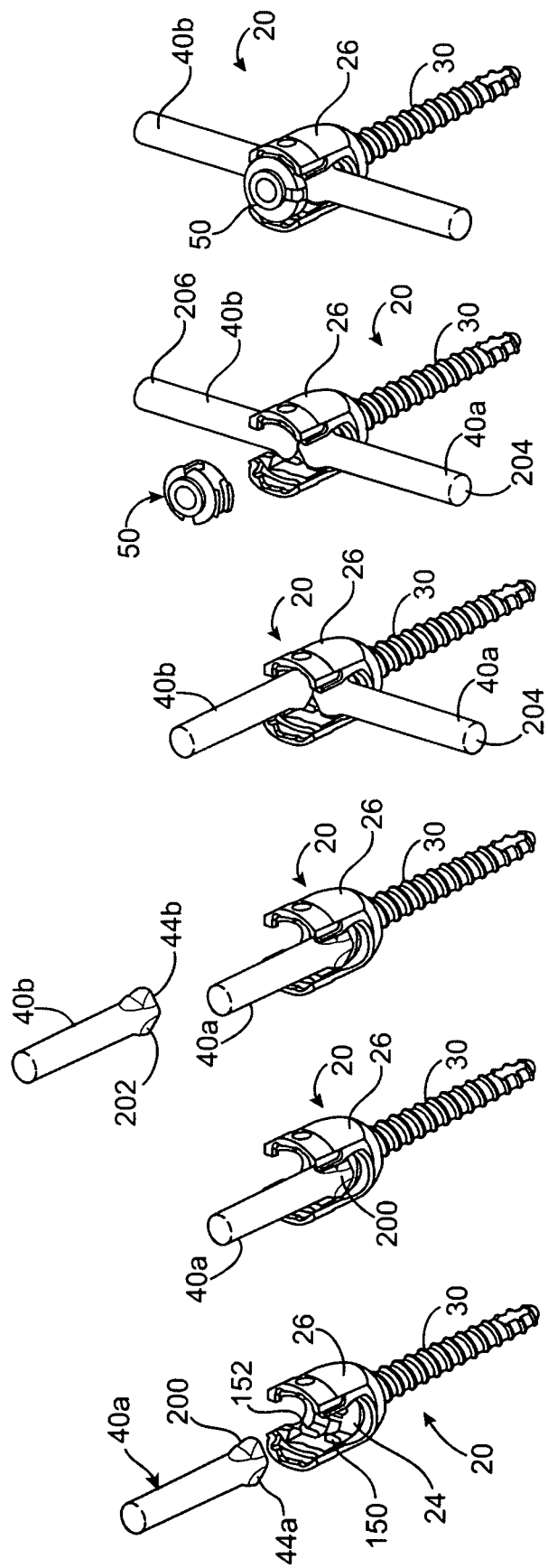

MULTI-LEVEL MINIMALLY INVASIVE SPINAL STABILIZATION SYSTEM

CROSS REFERENCE TO RELATED APPLICATIONS

This application claims priority to and is a continuation-in-part of U.S. Provisional Patent Application Ser. No. 60/920,872 entitled "Multi-level MIS system" filed on Mar. 30, 2007, hereby incorporated by reference in its entirety. This application is also a continuation-in-part of U.S. Provisional patent application Ser. No. 11/726,093 entitled "Screw systems and methods for use in stabilization of bone structures" filed on Mar. 20, 2007. This application is also a continuation-in-part of U.S. patent application Ser. No. 11/586,849 entitled "Systems and methods for stabilization of bone structures" filed on Oct. 25, 2006 which is a continuation-in-part of U.S. patent application Ser. No. 11/362,366 entitled "Systems and methods for stabilization of bone structures" filed on Feb. 23, 2006, which is a continuation-in-part of U.S. Patent Application Ser. No. 60/701,660 entitled "Systems and methods for stabilization of bone structures" filed on Jul. 22, 2005. This application is also a continuation-in-part of U.S. patent application Ser. No. 11/427,738 entitled "Systems and methods for stabilization of bone structures" filed on Jun. 29, 2006 which is a continuation-in-part of U.S. patent application Ser. No. 11/436,407 entitled "Systems and methods for posterior dynamic stabilization of the spine" filed on May 17, 2006 which is a continuation-in-part of U.S. patent application Ser. No. 11/033,452 entitled "Systems and methods for posterior dynamic stabilization of the spine" filed on Jan. 10, 2005 which is a continuation-in-part of U.S. patent application Ser. No. 11/006,495 entitled "Systems and methods for posterior dynamic stabilization of the spine" filed on Dec. 6, 2004 which is a continuation-in-part of U.S. patent application Ser. No. 10/970,366 entitled "Systems and methods for posterior dynamic stabilization of the spine" filed on Oct. 20, 2004. All of the above referenced patent applications are hereby incorporated by reference in their entireties.

FIELD

The present invention generally relates to surgical instruments and methods for using these instruments. More particularly, but not exclusively, minimally invasive methods of stabilizing one or more bone structures are disclosed.

BACKGROUND

Systems, methods and devices for stabilizing one or more bone structures of a patient have been available for many years. Prior art procedures typically require large incisions and also significant tissue manipulation to adequately expose the areas intended for the attachment. The procedures are associated with long recovery times and increased potential for adverse events, such as infection, usually associated with muscle and other tissue trauma and scarring.

Currently available minimally invasive techniques and products are limited. These procedures are difficult to perform, especially in spinal applications in which the attachment points are deeper in tissue, and damage to neighboring tissue must be avoided. Many of the currently available less invasive products remain somewhat invasive due to component configurations and required manipulations to be performed during the attachment.

In reference specifically to treatment of the spine, FIGS. 1A-1B illustrate a portion of the human spine having a superior vertebra 2 and an inferior vertebra 4, with an intervertebral disc 6 located in between the two vertebral bodies. The superior vertebra 2 has superior facet joints 8a and 8b, inferior facet joints 10a and 10b, posterior arch 16 and spinous process 18. Pedicles 3a and 3b interconnect the respective superior facet joints 8a, 8b to the vertebral body 2. Extending laterally from superior facet joints 8a, 8b are transverse processes 7a and 7b, respectively. Extending between each inferior facet joints 10a and 10b and the spinous process 18 are lamina 5a and 5b, respectively. Similarly, inferior vertebra 4 has superior facet joints 12a and 12b, superior pedicles 9a and 9b, transverse processes 11a and 11b, inferior facet joints 14a and 14b, lamina 15a and 15b, posterior arch 20, spinous process 22.

The superior vertebra with its inferior facets, the inferior vertebra with its superior facets, the intervertebral disc, and seven spinal ligaments (not shown) extending between the superior and inferior vertebrae together comprise a spinal motion segment or functional spine unit. Each spinal motion segment enables motion along three orthogonal axis, both in rotation and in translation. The various spinal motions are illustrated in FIGS. 1C-1E. In particular, FIG. 1C illustrates flexion and extension motions, anterior translation, and axial loading, FIG. 1D illustrates lateral bending motion and lateral translation motion and FIG. 1E illustrates rotation. A normally functioning spinal motion segment provides physiological limits and stiffness in each rotational and translational direction to create a stable and strong column structure to support physiological loads.

Various disorders of the spine can produce debilitating pain that can affect a spinal motion segment's ability to properly function. The specific location or source of spinal pain is most often an affected intervertebral disc or facet joint. Often, a disorder in one location or spinal component can lead to eventual deterioration or disorder, and ultimately, pain in the other.

Spine fusion (arthrodesis) is a procedure in which two or more adjacent vertebral bodies are fused together. While spine fusion generally helps to eliminate certain types of pain, it has been shown to decrease function by limiting the range of motion for patients in flexion, extension, rotation and lateral bending. Furthermore, the fusion creates increased stresses on adjacent non-fused motion segments and accelerated degeneration of the motion segments.

Various technologies and approaches have been developed to treat spinal pain without fusion in order to maintain or recreate the natural biomechanics of the spine. To this end, significant efforts are being made in the use of implantable artificial intervertebral discs. Unfortunately, the currently available artificial discs do not adequately address all of the mechanics of motion for the spinal column.

It has been found that the facet joints can also be a significant source of spinal disorders and debilitating pain. Current interventions for the treatment of facet joint disorders have not been found to provide completely successful results.

Most recently, surgical-based technologies, referred to as "dynamic posterior stabilization," have been developed to address spinal pain resulting from more than one disorder, when more than one structure of the spine have been compromised. An objective of such technologies is to provide the support of fusion-based implants while maximizing the natural biomechanics of the spine. Dynamic posterior stabilization systems typically fall into one of two general categories: (1) interspinous spacers and (2) posterior pedicle screw-based systems.

Examples of interspinous spacers are disclosed in U.S. Pat. Nos. Re. 36,211, 5,645,599, 6,695,842, 6,716,245 and 6,761,720.

Examples of pedicle screw-based systems are disclosed in U.S. Pat. Nos. 5,015,247, 5,484,437, 5,489,308, 5,609,636 and 5,658,337, 5,741,253, 6,080,155, 6,096,038, 6,264,656 and 6,270,498. These types of systems involve the use of screws which are positioned in the vertebral body through the pedicle. Certain types of these pedicle screw-based systems may be used to augment compromised facet joints, while others require removal of the spinous process and/or the facet joints for implantation. One such system, employs a cord which is extended between the pedicle screws and a fairly rigid spacer which is passed over the cord and positioned between the screws. While this system is able to provide load sharing and restoration of disc height, because it is so rigid, it is not effective in preserving the natural motion of the spinal segment into which it is implanted. Other pedicle screw-based systems employ joints between the pedicle screws that provide some discreet amounts of movement in different directions to somewhat simulate the complex movement of the spine.

There remains a need for minimally invasive methods and devices for bone stabilization procedures, including but not limited to dynamic spinal segment stabilization procedures and multi-level procedures for stabilizing more than two spinal segments. Furthermore, there is an ongoing need for systems that provide easier insertion for the clinician. Systems that allow simplified multiple degree of freedom of adjustment during implantation that then can be securely fixed are needed as are systems that can reduce fatigue failures, avoid large stresses between components under all load conditions and generally have a long implant life.

SUMMARY

According to one aspect of the invention, a spinal alignment system for interconnecting vertebral bodies is disclosed. The system includes a bone fastener polyaxially connected to a seat. The seat has a first rod receiving portion, a second rod receiving portion, a first rod channel and a second rod channel. A first and second rods that are configured to connect to the seat are provided and the seat is configured to connect to one end of a first rod at the first rod receiving portion and to one end of a second rod at the second rod receiving portion such that the first rod is movable into a position projecting through the first rod channel and the second rod is movable into a position projecting through the second rod channel. At least one of the first and second rods is polyaxially movable with respect to the seat while in a position projecting through a respective rod channel. The system is implanted into a first vertebral body and the first rod is dimensioned to span between the first vertebral body and a second vertebral body where a second system is implanted with the first rod being seated in the second system. The second rod is dimensioned to span between the first vertebral body and a third vertebral body where a third system is implanted with the second rod being seated in the third system. A closure mechanism is provided to cap the top opening of the first system and lock the polyaxial motion of the first and second rods with respect to the seat and simultaneously or independently lock the polyaxial motion of the bone fastener with respect to the seat. Additional closure mechanisms cap the second and third systems to retain the second ends of the rods therein.

According to another aspect of the invention, a spinal alignment system for interconnecting vertebral bodies is provided. The system includes a first bone fastener configured for spinal engagement into a first vertebra. The first bone fastener is connected to a first seat that has at least a first rod channel and a first top opening. The system further includes a second bone fastener configured for spinal engagement into a second vertebra. The second bone fastener is connected to a second seat that has a first rod receiving portion and a second rod receiving portion, a second rod channel and a third rod channel and a second top opening. The system further includes a third bone fastener configured for spinal engagement into a third vertebra. The third bone fastener is connected to a third seat that has at least a fourth rod channel and a third top opening. A first rod having a first end and a second end is provided. The first end of the first rod is configured to connect to the first rod receiving portion of the second seat. A second rod having a first end and a second end is provided. The first end of the second rod is configured to connect to the second rod receiving portion of the second seat. The second seat is configured to connect to the first end of the first rod at the first rod receiving portion and to first end of the second rod at the second rod receiving portion such that the first rod is movable into a position projecting through the second rod channel into the first rod channel and the second rod is movable into a position projecting through the third rod channel into the fourth rod channel. At least one of the first and second rods is polyaxially movable with respect to the second seat while in a position projecting through a respective rod channel. A first closure mechanism configured to close the first top opening to secure the first rod in the first seat is provided. A second closure mechanism that is configured to close the second top opening and lock the polyaxial motion of the at least one of the polyaxially movable first and second rods in a position within the range of polyaxial motion is also provided. A third closure mechanism configured to close the third top opening to secure the second rod in the third seat is provided. The second closure mechanism is configured lock the polyaxial motion of the second bone fastener with respect to the second seat simultaneously or independently of locking the polyaxial motion of the at least one of the polyaxially movable first and second rods.

According to yet another aspect of the invention, a method is provided. A first bone screw system is provided. The first bone screw system includes a first bone screw connected to a first seat. The first seat has a first rod channel, a second rod channel and a first top opening. The first bone screw system further includes a first closure mechanism configured to close the first top opening. The first seat is configured to connect with a first rod and a second rod. The first bone screw system is implanted into a first vertebral body. A first rod having a first end and a second end is provided. The first end of the first rod is configured for connection to the first seat. The first rod is introduced into the first seat through the first top opening in a first orientation. The first end of the first rod is connected to the first seat. A second rod having a first end and a second end is provided. The first end of the second rod is configured for connection to the first seat. The second rod is introduced into the first seat through the first top opening in a first orientation. The first end of the second rod is connected to the first seat. The first rod is moved into a second orientation such that the first rod projects through the first rod channel. The second rod is moved into a second orientation such that the second rod projects through the second rod channel. The first closure mechanism is inserted into the first top opening. The polyaxial motions of first and second rods are locked via the first closure mechanism. The motion of the first bone screw relative to the first seat is also locked via the first closure mechanism either simultaneously or independently of the polyaxial motions of the first and second rods relative to the first seat.

Advantages of the invention may include one or more of the following. Insertion of certain of the described screws and pivoting rods may be performed with reduced insertion forces, and may feature simplified usage. Rotational locking may be employed to secure the pivoting rod against movement. Embodiments of the invention allow reduced stress on the pivoting rod. Embodiments of the invention are compatible with other pedicle screw systems and/or spinal implants. Embodiments of the invention may be applicable to patients with degenerative disc disease, spinal stenosis, spondylolisthesis, spinal deformities, fractures, pseudarthrosis, tumors, failed prior fusions, or other vertebral segment trauma and disease.

It is noted that perfect alignment of the screws with one another is quite difficult and requires great skill on the part of the surgeon to accomplish. Alignment of the screws is even more difficult in minimally invasive/percutaneous procedures. Alignment may further be complicated by the patient's condition such as damaged or diseased bone or other anatomical condition. Screws can be out-of-alignment not only in one plane but in two and in some cases three planes. However, the polyaxial seat of the screw and of the pivoting rod of the present invention advantageously allows the seat to swivel on top of the screw and the pivoting rod to swivel with respect to the seat such that they may be lined up in the most difficult of orientations of the screws' axes and can even thus be made to accommodate a certain amount of screw misalignment from difference in height once they are inserted into bone. The polyaxial motion of the seat and of the pivoting rods allow the rod channels to be more easily lined-up so that the rod can be placed or attached between the screws without having their axes perfectly aligned to do so. Then the seat can be locked down to eliminate motion and stabilize one or more vertebral segments. Another advantage of the present invention over other systems that interconnect multiple spinal levels with a single rod is that the present invention interconnects multiple levels without using a single rod on one side of the spine but employs N−1 rods where N is the number of levels or number of spinal vertebrae interconnected. Using N−1 number of rods in a system of the present invention that allows polyaxial motion of each rod with respect to the seat and allows each rod to be locked into position at an angle in more than one plane reduces the stresses exerted on vertebrae relative to a system employing a single straight or curved rod spanning multiple levels. The multiple polyaxial rods used in the system are configured to conform to the lordosis of the spine.

Other advantages will be apparent from the description that follows, including the drawings and claims.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 14A illustrates a perspective view of a first pivoting rod vertically positioned in juxtaposition to a screw system according to the present invention.

FIG. 14B illustrates a perspective view of a first pivoting rod connected to a screw system according to the present invention.

FIG. 14C illustrates a perspective view of a first pivoting rod connected to a screw system and a second pivoting rod in juxtaposition to the screw system according to the present invention.

FIG. 14D illustrates a perspective view of a first pivoting rod connected to a screw system and pivoted outwardly from a vertical orientation and a second pivoting rod connected to the screw system according to the present invention.

FIG. 14E illustrates a perspective view of a first pivoting rod connected to a screw system and pivoted outwardly from a vertical orientation and a second pivoting rod connected to the screw system and pivoted outwardly from a vertical orientation and a closure mechanism in juxtaposition to the screw system according to the present invention.

FIG. 14F illustrates a perspective view of a first pivoting rod connected to a screw system and pivoted outwardly from a vertical orientation and a second pivoting rod connected to the screw system and pivoted outwardly from a vertical orientation and a closure mechanism connected to the screw system according to the present invention.

DETAILED DESCRIPTION

Before the subject devices, systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a spinal segment" may include a plurality of such spinal segments and reference to "the screw" includes reference to one or more screws and equivalents thereof known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Figure 1A:
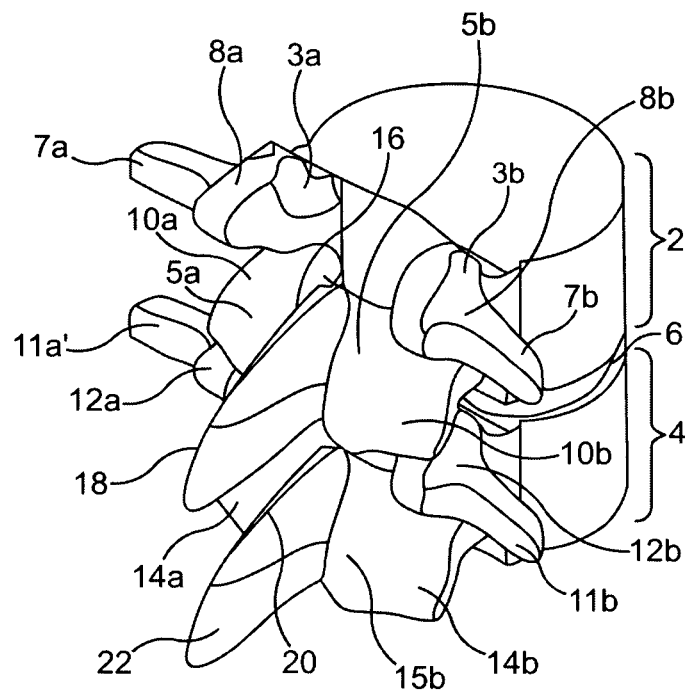
FIGS. 1A and 1B illustrate perspective views of a portion of the human spine having two vertebral segments, where the spinous process and the lamina of the superior vertebra have been resected in FIG. 1B.
Figure 1B:
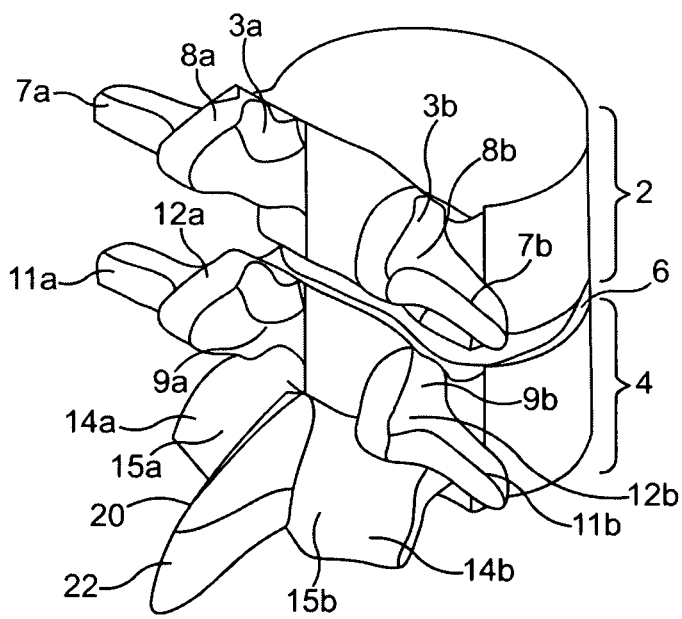
Figure 1C:
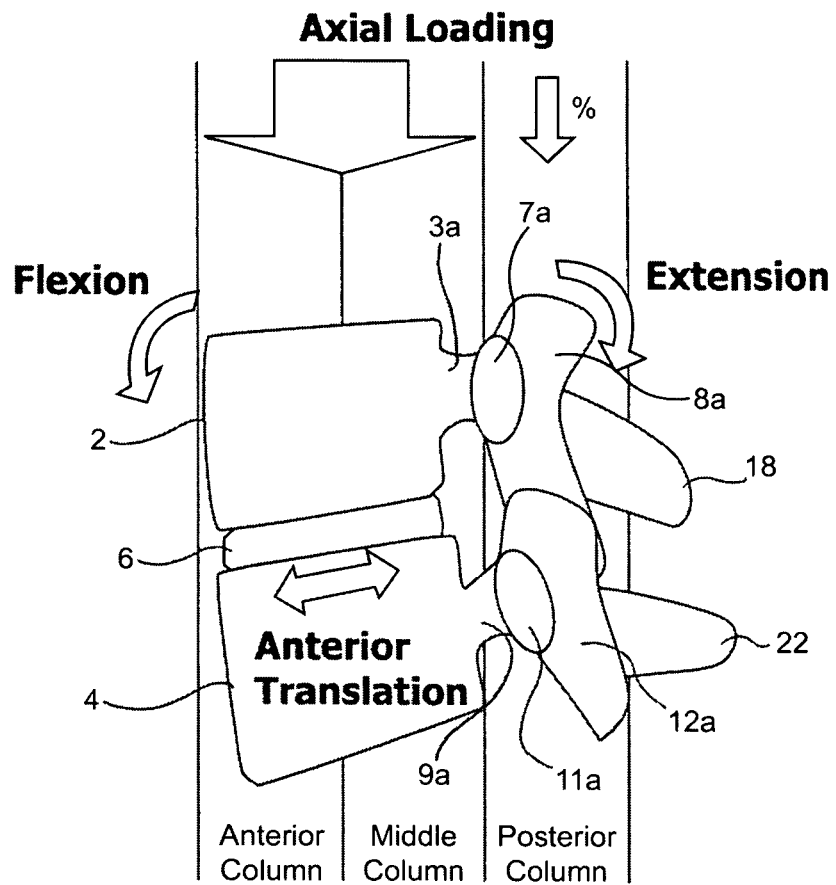
FIGS. 1C, 1D and 1E illustrate left, dorsal and top views, respectively, of the spinal segments of FIG. 1A-1B undergoing various motions.
Figure 1D:
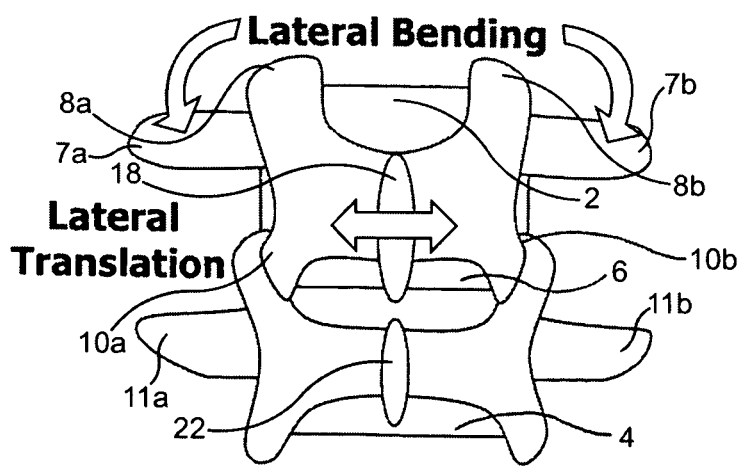
Figure 1E:
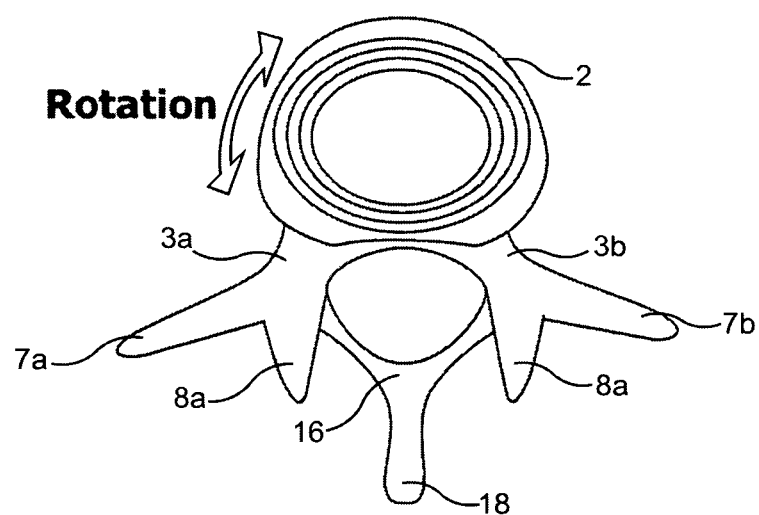

The present invention will now be described in greater detail by way of the following description of exemplary embodiments and variations of the systems and methods of the present invention. While more fully described in the context of the description of the subject methods of implanting the subject systems, it should be initially noted that in certain applications where the natural facet joints are compromised, inferior facets 10*a* and 10*b*, lamina 5*a* and 5*b*, posterior arch 16 and spinous process 18 of superior vertebra 2 of FIG. 1A may be resected for purposes of implantation of certain of the dynamic stabilization systems of the present invention. In other applications, where possible, the natural facet joints, lamina and/or spinous processes are spared and left intact for implantation of other dynamic stabilization systems of the present invention.

It should also be understood that the term "system", when referring to a system of the present invention, most typically refers to a set of components which includes multiple bone stabilization components such as a superior, cephalad or rostral (towards the head) component configured for implantation into a superior vertebra of a vertebral motion segment and an inferior or caudal (towards the feet) component configured for implantation into an inferior vertebra of a vertebral motion segment. A pair of such component sets may include one set of components configured for implantation into and stabilization of the left side of a vertebral segment and another set configured for the implantation into and stabilization of the right side of a vertebral segment. Where multiple bone segments such as spinal segments or units are being treated, the term "system" may refer to two or more pairs of component sets, i.e., two or more left sets and/or two or more right sets of components. Such a multilevel system involves stacking of component sets in which each set includes a superior component, an inferior component, and one or more medial components therebetween.

The superior and inferior components (and any medial components therebetween), when operatively implanted, may be engaged or interface with each other in a manner that enables the treated spinal motion segment to mimic the function and movement of a healthy segment, or may simply fuse the segments such as to eliminate pain and/or promote or enhance healing. The interconnecting or interface means include one or more structures or members that enables, limits and/or otherwise selectively controls spinal or other body motion. The structures may perform such functions by exerting various forces on the system components, and thus on the target vertebrae. The manner of coupling, interfacing, engagement or interconnection between the subject system components may involve compression, distraction, rotation or torsion, or a combination thereof. In certain embodiments, the extent or degree of these forces or motions between the components may be intraoperatively selected and/or adjusted to address the condition being treated, to accommodate the particular spinal anatomy into which the system is implanted, and to achieve the desired therapeutic result.

In certain embodiments, the multiple components, such as superior and inferior spinal components, are mechanically coupled to each other by one or more interconnecting or interfacing means. In other embodiments, components interface in a manner that constrains their relative movement and enables the treated segment to mimic the function or partial function and/or movement or partial movement of a healthy segment. Typically, spinal interconnecting means is a dorsally positioned component, i.e., positioned posteriorly of the superior and inferior components, or may be a laterally positioned component, i.e., positioned to the outer side of the posterior and inferior components. The structures may include one or more struts and/or joints that provide for stabilized spinal motion. The various system embodiments may further include a band, interchangeably referred to as a ligament, which provides a tensioned relationship between the superior and inferior components and helps to maintain the proper relationship between the components.

Reference will now be made in detail to the present embodiments of the invention, examples of which are illustrated in the accompanying drawings. Wherever possible, the same reference numbers will be used throughout the drawings to refer to the same or like parts. In addition, each of the inventive embodiments described herein may be employed in a percutaneous procedure, a mini-open procedure or an open procedure. Utilization of minimally invasive techniques can shorten the procedure's time and speed recovery by the patient. The application of these inventions in a minimally invasive manner is not a requirement.

Figure 2A:
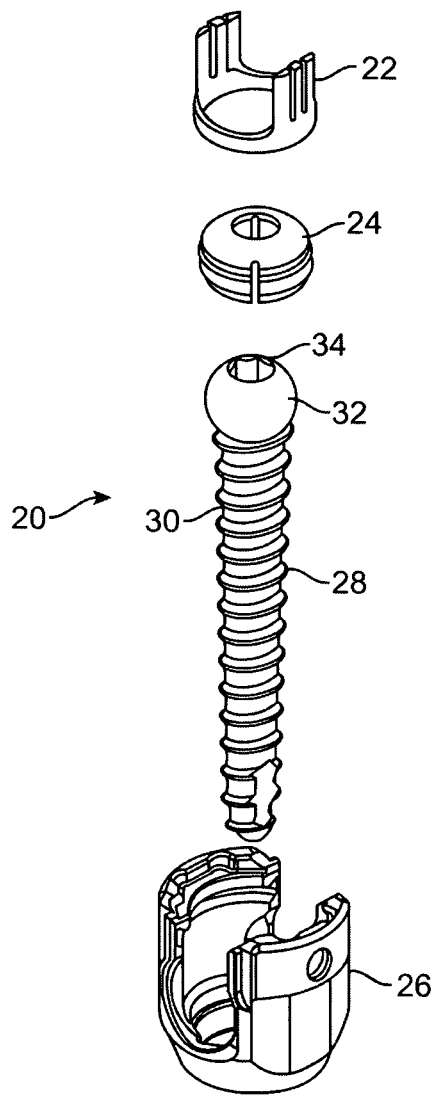
FIG. 2A illustrates a perspective exploded view of a screw system which may be employed in an embodiment of the present invention.
Figure 2B:
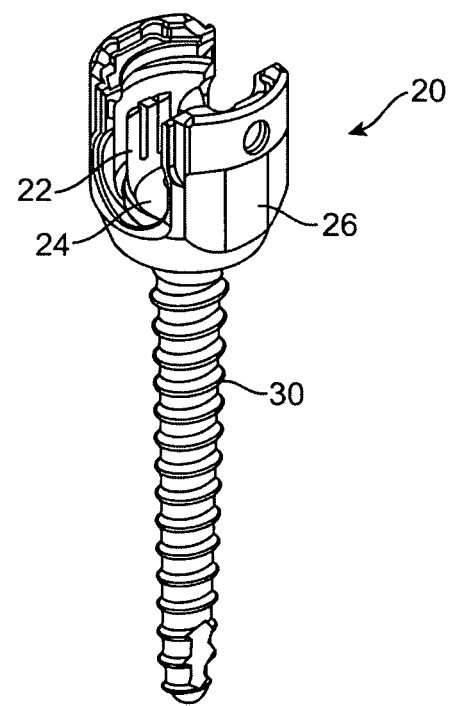
FIG. 2B illustrates a perspective view of an assembled screw system of the present invention.

FIG. 2A illustrates a perspective exploded and perspective view of a screw system which may be employed in an embodiment of the present invention and FIG. 2B illustrates a perspective view of an assembled screw system. The screw system 20 is shown having a screw 30 with threads 28, retaining ring 22, a coupler 24, and seat 26. The screw system 20 includes a closure or locking mechanism (not shown) for capping the open end of the seat 26. The threads 28 are appropriate for entering the bone of a patient. At a proximal end of screw 30 is a ball end 32. While a ball end 32 is shown, various other shapes may also be employed. A hex socket 34 that is interconnected with a guidewire lumen (not shown) extends through the general axial center of screw 30 and also can extend through the retaining ring 22, coupler 24 and seat 26. The system is suitable for being installed in a patient for treating at least one or more of the following: degenerative disc disease, spinal stenosis, spondylolisthesis, spinal deformities, fractures, pseudarthrosis, tumors, failed previous fusions, other vertebral segment trauma or diseases.

The ball end 32 of screw 30 is fitted into the bottom of the coupler 24, which has a spherical interior shape, as will be described in greater detail below. If end 32 has a different shape, the shape of the interior of the bottom of the coupler 24 may be similarly complimentary. No matter the shape, when the ball end is fitted into the bottom end of end of the coupler 24, the coupler 24 may be fitted into the "bucket-shaped" seat 26. The retaining ring 22 ensures that the coupler 24 does not escape from the interior of seat 26, and is pressed between the coupler 24 and seat 26 and is described in greater detail below.

Figure 3A:
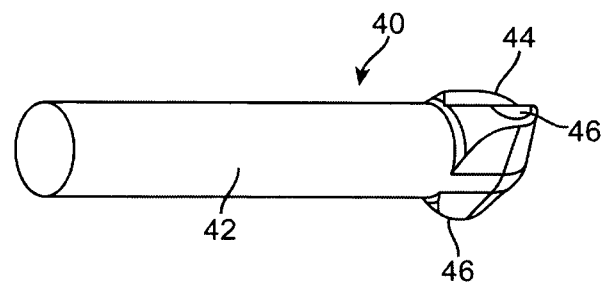
FIG. 3A illustrates a perspective view of a pivoting rod of the present invention.

FIG. 3A illustrates a perspective view of a rod 40 which is employed in an embodiment of the present invention. FIGS. 3B-3E illustrate side, bottom, top and end views of the pivoting rod 40, respectively. The rod 40 in FIGS. 3A-3E is shown to be straight. In another variation, a curved pivoting rod that conforms to the natural curve of the spine is employed. The rod 40 has a shaft 42, a connecting end 44, and two contacts 46 (one of which is not shown in FIG. 3B) for connection with the screw system 20. The shaft 42 may vary in length, or may be adjustable by the physician, either by a telescoping mechanism or by being cut to measure. The end of the shaft 42 opposite that of connecting end 44 may be straight, as shown, or may itself incorporate a second connecting end (not shown) or other type of end to enable trapping and capture in a seat of a pedicle screw system 20 mounted to another spinal segment. The connecting end 44 may be approximately ball-shaped, square or rectangular solid, or other such shape, so long as the shape allows movement of the rod with respect to the seat 26 in at least one plane.

In general, the rod 40 and the screw system 20 include mating features adapted to connect each other together. In particular, the mating features on the screw system 20 can be located on the seat 26, on the retaining ring 22 as with respect to the variation of FIGS. 2A-B, and/or on the coupler 24 as with respect to the variation of FIG. 9A.

Figure 3B:
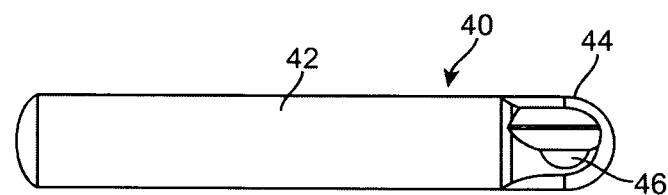
FIG. 3B illustrates a side view of a pivoting rod of the present invention.
Figure 3C:
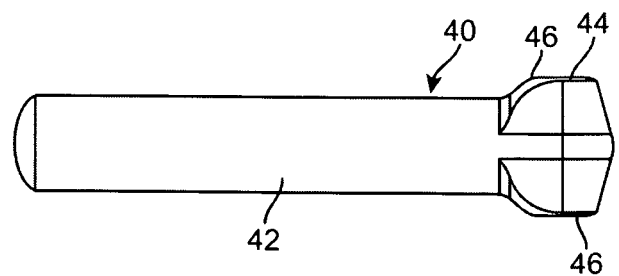
FIG. 3C illustrates a bottom view of a pivoting rod of the present invention.
Figure 3D:
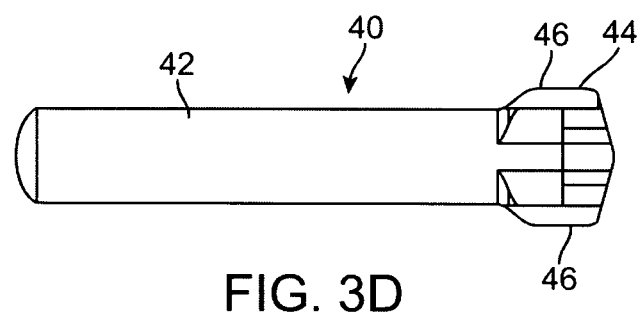
FIG. 3D illustrates a top view of a pivoting rod of the present invention.
Figure 3E:
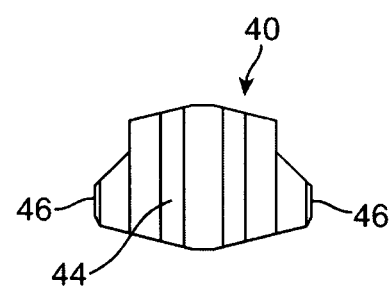
FIG. 3E illustrates an end view of a pivoting rod of the present invention.

As shown in FIG. 3B, the contacts 46 of the connecting end are flattened. The flat contacts 46 assist in confining the range of motion of the rod substantially within a single plane. Furthermore, the flattened contacts 46 provide for a greater surface area that is in contact with the screw system 20 and thereby create an advantageous snug-fit engagement therewith. Because of the flattened sides 46, when the rod 40 is inserted, the greater surface area of contact of the flattened sides 46 with the screw system 20 provides for a snug-fit engagement that would otherwise be the case with a more rounded rod end that would permit greater angulation. As a result of the flattened sides, the rod advantageously does not pivot on its own in a direction away from the insertion angle or other angle at which the rod is positioned subsequent to insertion into the screw system 20. This feature facilitates insertion for the surgeon.

In another variation, the contacts 46 are not flattened but are rounded such that the pivoting rod 40 is capable of polyaxial motion, pivoting side-to-side, or laterally, left-to-right in addition to vertical-to-horizontal or horizontal-to-vertical which will be described in greater detail below with respect to another variation of the invention.

Figure 4A:
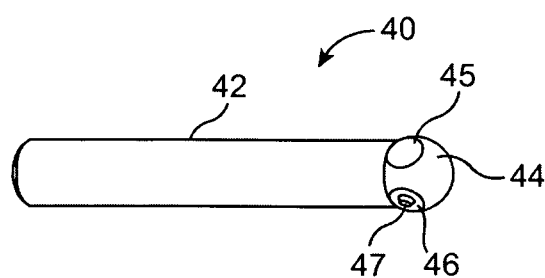
FIG. 4A illustrates a perspective view of another variation of a pivoting rod of the present invention.

In another variation of the pivoting rod 40 shown in FIG. 4A, the contacts 46 include pins 47 for engaging with the screw system 20. Additional flat portions 45 are formed on the connecting end 44 of the rod 40 which is more ball-shaped than the rod 40 of FIGS. 3A-3E. The flat portions 45 are substantially perpendicular to the flattened contacts 46 on the connecting end 44. The pins 47 are substantially parallel to the flat portions 45. When the rod 40 is inserted into the seat 26 via the retaining ring 22 and pivoted into a generally horizontal position, the flat portions 45 face upwardly and downwardly and as a result provide a lower profile for the rod within the seat. Furthermore, the flat portions 45 provide a flat contact surface for the locking mechanism or set screw on the upper surface of the rod 40 and a flat contact surface for the coupler 24 on the bottom surface of the rod 40. The rod 40 may have more than two flat portions 45 and/or two flattened contacts 46 and any number and combination of flat portions 45 and contacts 46 are within the scope of the present invention. An alternative way in which the pivoting rod 40 may be attached to the screw system 20 that employs pins is such that the set of two pins 47 mate with a corresponding set of holes in the screw system 20. The pins 47 may be spring-loaded with springs. This spring-biased pin allows pivoting of the rod 40 and also allows the pin to move radially inward during insertion, and then "pop" out when in place. The pin may then be retracted for removal of the rod 40. In an alternative embodiment, the pin may be permanently locked in place by injecting cement or glue or another such material into the travel volume of the pin.

Figure 4B:
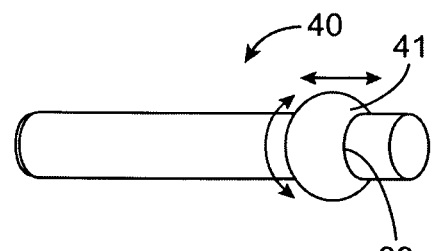
FIG. 4B illustrates a perspective view of another variation of a pivoting rod of the present invention.

Still referencing FIG. 4A, the rod 40 is shown with integral pins 47 that are configured to snap-fit with the screw system 20 to secure the rod 40 in place and permit movement of the rod 40 with respect to the seat 26. In one variation, the pins 46 are chamfered to ease the insertion of the rod 40 by the clinician into the screw system 20 and also ease removal of the rod 40 from the screw system 20, if desired. Pins are not the only means of attachment of the rod 40 to the screw system 20 and other variations and means are within the scope of the invention. For example, as shown in FIG. 4B, the connecting end 44 of a rod 40 is provided with a ball portion 41 having a bore 39 passing through it. The rod 40 of FIG. 4B is positioned inside the bore 39 of the ball portion 41 such that the ball portion 41 is allowed to rotate and slide relative to the rod as indicated by the arrows in FIG. 4B. This embodiment advantageously provides yet another degree of freedom of motion and facilitates installation by the surgeon. Furthermore, the embodiment of FIG. 4B advantageously permits the polyaxial bone screw 30 to be locked into position independently of rod 40 and in another variation it permits the rod 40 to be locked into position independently of the bone screw 30. More details of the independent lock down capability of this embodiment will be described in greater detail hereinbelow.

Figure 5A:
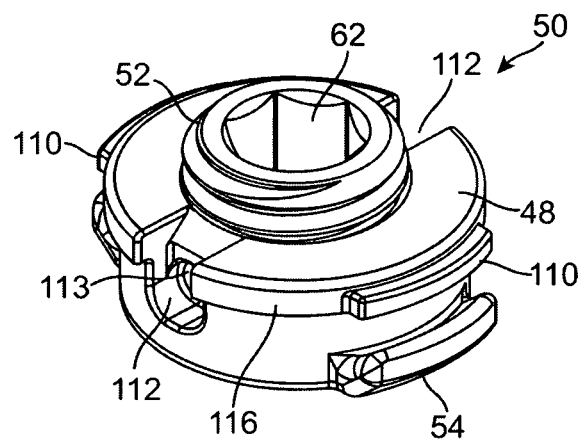
FIG. 5A illustrates a perspective view of a locking mechanism of a screw system of the present invention.
Figure 5B:
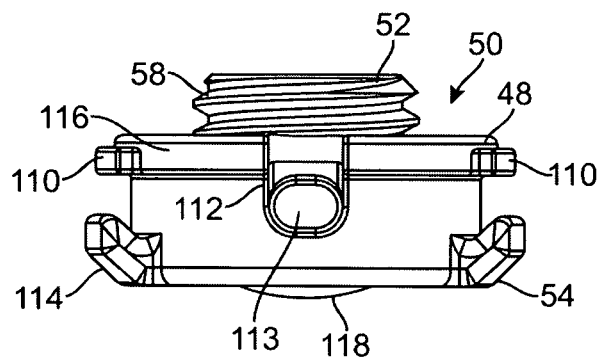
FIG. 5B illustrates a side view of a locking mechanism of a screw system of the present invention.
Figure 5C:
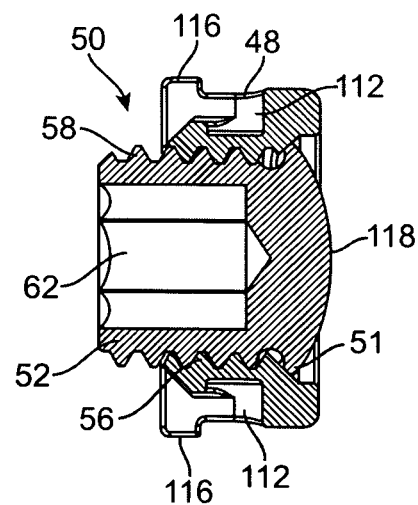
FIG. 5C illustrates a cross-sectional view of a locking mechanism of a screw system of the present invention.

FIGS. 5A-5C illustrate perspective, side and cross-sectional views, respectively, of a closure mechanism 50. The closure mechanism is shown as a cap and set screw system 50 which may be employed in an embodiment of the present invention as part of the screw system 20. It should be noted that the closure mechanism is not limited to a cap and set screw combination as shown and described herein and various other closure mechanisms evident to a person having ordinary skill in the art are within the scope of the invention. Some examples of closure mechanisms include but are not limited to a threaded closure mechanism having external threads that engage with a threaded internal portion of the seat, a sliding closure mechanism, a compression fit closure mechanism, and a snap-fit closure mechanism to name a few. The closure mechanism 50, when fully installed in the seat 26, secures the rod 40 against movement. In one variation, the closure or locking system 50 includes a cap 48 and a set screw 52. The cap 48 includes a set screw receiving portion generally located along a central bore of the cap 48. The cap 48 and set screw 52 are configured to close the top opening of the seat 26. The external shape of the cap 48 is substantially cylindrical and configured to fit into the open end of the seat 26. The cap 48 includes a top surface and a bottom surface interconnected by an outer surface and an inner surface. The cap 48 includes external flanges or features 54, discussed in more detail below, and internal screw threads 56.

The set screw 52 includes external screw threads 58 and a socket 62 for a driving tool, the socket 62 being substantially coaxial with the screw threads 58. The set screw 52 also includes a flange 51 (FIG. 5C) at the bottom end of the set screw 52. The flange 51 is configured to extend outwardly from the circumference of the set screw 52 to serve as a stop and to prevent the set screw 52 from being backed-out as the set screw 52 is retracted upwardly with respect to the cap 48.

Various aspects and alternative embodiments of this basic system are described below. In this regard, it is noted that the above system of FIGS. 2A-5C would typically be employed in the following fashion: Each screw system includes a bone fastener such as a bone screw, a seat, and a closure mechanism. A first screw system would be installed in a first vertebral body of a patient's spine, this first screw system having a connection for attaching to a first end of the rod. A second screw system would also be installed in a second vertebral body of a patient's spine that is preferably adjacent to the first vertebral body, this second screw system having a receiving portion or seat that receives the second end of the rod. When connected to the connection of the first screw system, the rod is pivoted or rotated such that the second end of the rod is seated in the second screw system. Generally, the seat is capable of movement in at least one plane with respect to the screw and the rod is capable of movement in at least one plane with respect to the seat. A first closure mechanism is employed to secure the first end of the rod in the first seat and a second closure mechanism is employed to secure the second end of the rod in the second seat. The closure mechanism may be configured to (1) to lock movement of the seat with respect to the screw while permitting movement of the rod with respect to the seat, (2) to lock movement of the rod with respect to the seat while permitting movement of the seat with respect to the screw, (3) to lock movement of the seat with respect to the screw while permitting movement of the rod with respect to the seat and with further actuation of the closure mechanism to lock movement of the rod with respect to the seat, (4) to lock movement of the rod with respect to the seat while permitting movement of the seat with respect to the screw and with further actuation of the closure mechanism to lock movement of the seat with respect to the screw, (5) to lock movement of the seat with respect to the screw independently of locking the movement of the rod with respect to the seat, (6) to lock movement of the seat with respect to the screw simultaneously with locking the movement of the rod with respect to the seat, and (7) to secure the rod inside the seat while permitting limited dynamic movement of the rod with respect to seat and permitting limited dynamic movement of the seat with respect to the screw. The first screw system and second screw system are identical in one variation. Other parts of the screw systems may be the same and/or interchangeable and various connection means may be employed such as described in this invention, including but not limited to use of a coupler and retaining ring. Further, the pivoting rod may include a dynamic element at some point along its length if desired, as described, e.g., in U.S. patent application Ser. No. 11/427,738, filed Jun. 29, 2006, U.S. patent application Ser. No. 10/970,366 filed Oct. 20, 2004, U.S. patent application Ser. No. 11/006,495 filed Dec. 6, 2004, U.S. patent application Ser. No. 11/033,452 filed Jan. 10, 2005, U.S. patent application Ser. No. 11/436,407 filed on May 17, 2006, U.S. Provisional Patent Application Ser. No. 60/931,811 filed May 25, 2007, U.S. Patent Application Ser. No. 60/994,899 filed on Sep. 21, 2007, and U.S. Patent Application Ser. No. 61/063,878 filed on Feb. 6, 2008 all of which are incorporated by reference herein in their entireties for all purposes.

Figure 6A:
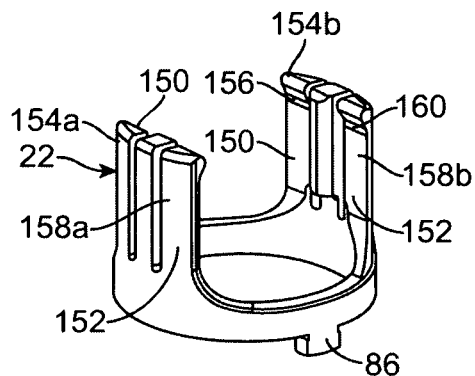
FIG. 6A illustrates a perspective view of a retaining ring according to the present invention.
Figure 6B:
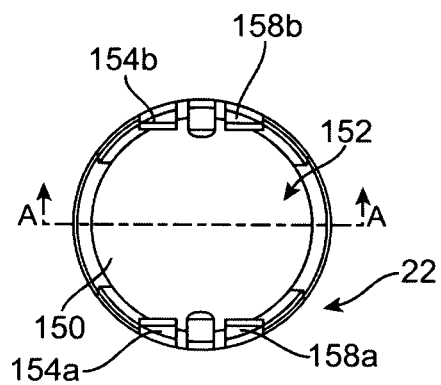
FIG. 6B illustrates a top view of a retaining ring according to the present invention.
Figure 6C:
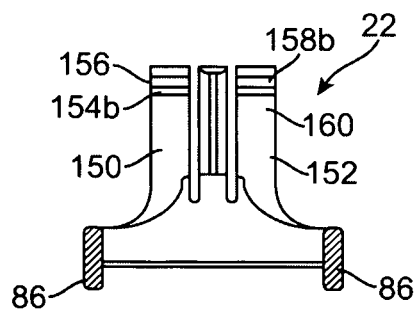
FIG. 6C illustrates a side cross-sectional view of a retaining ring according to the present invention.

Various aspects of the seat, coupler, and retaining ring will now be discussed. Referring to FIGS. 6A-6C, a retaining ring 22 is shown. Retaining ring 22 is shown with two projections 86, also known as keys, which engage features on the seat 26, to hold the retaining ring 22 in place. The retaining ring 22 may include a split such that the retaining ring 22 is approximately C-shaped when viewed from above. One or more such splits may be formed. The retaining ring 22 presses into place inside the seat 26 and is generally pressed between the coupler 24 and seat 26 in a press or snap fit engagement to secure the retaining ring 22, coupler 24, seat 26 and screw 30.

Still referencing FIGS. 6A-6C, the retaining ring 22 includes at least one rod receiving portion 150. The variation in FIGS. 6A-6C includes a first rod receiving portion 150 and a second rod receiving portion 152 adjacent to each other. Each of the first and second rod receiving portions 150, 152 are a pair of upstanding forks extending from a substantially annular base that may or may not include one or more splits described above. The first rod receiving portion 150 includes a pair of upstanding prongs 154a, 154b which together are configured to retain a first pivoting rod. The first rod receiving portion 150 is configured to retain the first pivoting rod in a press-fit, friction fit, slot and pin engagement or any other suitable engagement means that permits the rod to rotate, pivot or otherwise move in at least one plane while retained within the first rod receiving portion 150. In one variation, each prong 154a, 154b includes an undercut 156 that helps to retain the rod in place. Similar to the first rod receiving portion 150, the second rod receiving portion 152 includes a pair of upstanding prongs 158a, 158b which together are configured to retain a second pivoting rod. The second rod receiving portion 152 is configured to retain the second pivoting rod in a press-fit, friction fit, slot and pin engagement or any other suitable engagement means that permits the rod to rotate, pivot or otherwise move in at least one plane while retained within the second rod receiving portion. In one variation, each prong 158a, 158b includes an undercut 160 that helps to retain the rod in place. In one variation, the inner surface of the prongs is flat such that when mated with the rod, the flat surfaces restrain articulation of the rod in one plane. The prongs are allowed to flex slightly to retain the rods and allow the rods to move in at least one plane such as up-and-down, side-to-side, polyaxially or in a limited or constrained polyaxial motion. Slots in the retaining ring or coupler also allow the coupler or retaining ring to flex allowing the rod to articulate in a narrow plane. The retaining ring 22 is configured to receive and retain securely two rods, side-by-side within one seat 26 of one screw system for a multi-level application in which at least three vertebrae are interconnected. The retaining ring 22 that is configured to receive two rods may also be employed to receive one rod in a single level application in which two adjacent vertebrae are interconnected. In such an application, the rod is preferably pivoted away from the adjacent rod channel 90a (see FIG. 19A) in the seat 26a and towards the opposite rod channel 90b (see FIG. 19A) in the same seat 26a as will be described in greater detail below with respect to FIG. 19A.

Figure 7A:
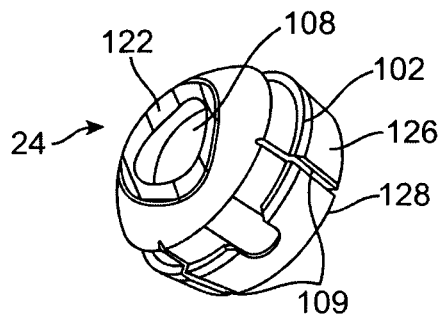
FIG. 7A illustrates a perspective view of a coupler according to the present invention.
Figure 7B:
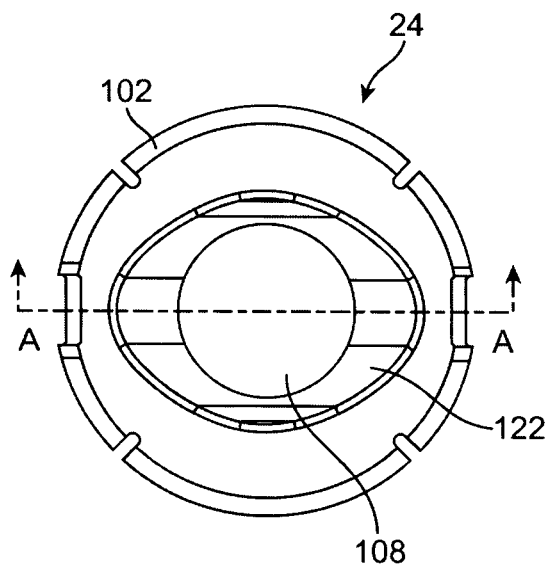
FIG. 7B illustrates a top view of a coupler according to the present invention.
Figure 7C:
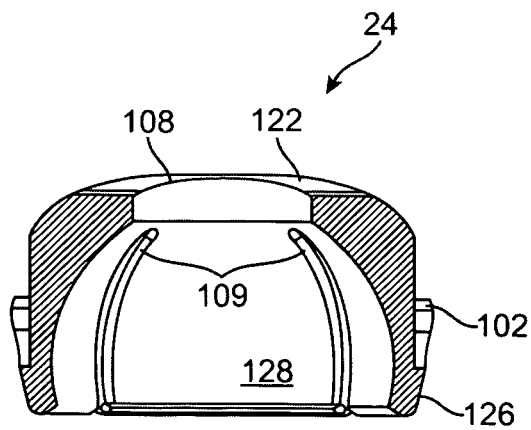
FIG. 7C illustrates side cross-sectional view along line A-A of FIG. 7B of a coupler according to the present invention.

FIGS. 7A-7C show additional details of the coupler 24. The coupler 24 generally has a bone screw receiving portion 128 and a rod receiving portion 122. The bone screw receiving portion 128 is substantially domed shaped to correspond to the shape of the ball end 32 of the screw 30 received therein. The rod receiving portion 122 is shown in one variation as a beveled region. The coupler access bore hole 108 provides access to the engagement means of the screw such as a hex socket. The inner surfaces of the rod receiving portion 122 of the coupler 24 and the screw head receiving portion 128 are provided with grit-blasting to increase the surface roughness and resultant friction coefficient between the coupler and/or the rod.

Still referencing FIGS. 7A-7C, a lip 102 is provided to mate with the retaining ring 22. An approximately spherical bore 128 or screw head receiving portion is provided in the interior of the bottom of the coupler 24 that "snap-fits" over the head 32 of the screw 30 to allow a limited amount of rotation, for example 60 degrees of polyaxial rotation of the screw with respect to the coupler. The exterior surface of the coupler 24, exterior of the spherical bore 128, may be a generally tapered ramp 126. Slits 109 may further be provided to allow circumferential compression around the screw head 32.

Figure 8A:
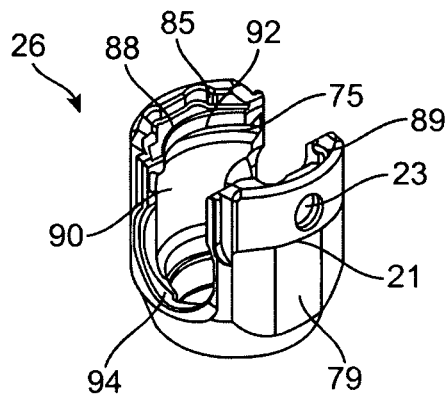
FIG. 8A illustrates a perspective view of a seat according to the present invention.
Figure 8B:
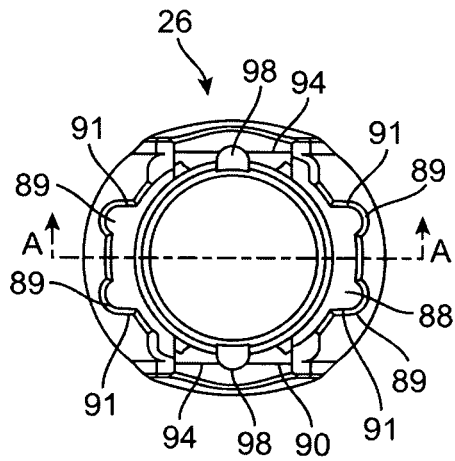
FIG. 8B illustrates a top view of a seat according to the present invention.
Figure 8C:
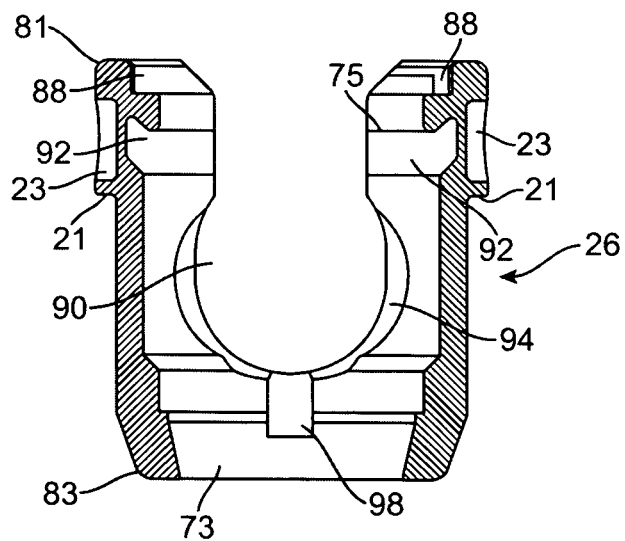
FIG. 8C illustrates a side cross-sectional view along line A-A of FIG. 8B of a seat according to the present invention.

Referring now to FIGS. 8A-8D, the seat 26 includes an inner surface and an outer surface and a first end 81 and a second end 83. At least one sidewall 79 extends between the first end 81 and the second end 83 forming a top opening at the first end 81 and at least one "U"-shaped void or rod channel 90 into which the rod may pivot when installed. Two rod channels 90 or voids are shown in FIGS. 8A-8C in which voids 90 are defined in part by seat rod channel bevels 94 for allowing increased polyaxial movement of the rod with respect to the seat 26. A void or keyway 98 is provided near the base of the seat to engage each projection 86 to orient the retaining ring 22 in a press-fit fashion with respect to a conforming space in the coupler 24 and seat 26. In FIG. 8B, the keyways 98 are adjacent the rod channel bevels 94. The retaining ring and seat rod channel bevels may generally match each other in shape, pitch, angle, slope, etc., and assist in orienting the rod pivot arc as well as orienting the rod channel to receive the rod.

The seat 26 includes a closure mechanism receiving portion or a cap receiving portion 75 configured to receive a cap 48 at the first end 81 and a coupler receiving portion 73 configured to receive a coupler 24. The coupler receiving portion 73 includes a tapered ramp that corresponds to a tapered ramp on the coupler 24. The cap receiving portion 75 includes a locking lug groove 88 that is provided near the top of the seat 26 to slidingly receive a corresponding locking lug or projection of the cap, described below. Cap rotation of, for example 90 degrees, secures the cap in place. The locking lug groove 88 may further include an anti-rotation mechanism, such as a mechanical stop. In this way, the locking lugs may be fixed in the amount of rotation needed to secure them in place. A wing groove 92 is also provided on the seat 26, to slidingly receive and engage a corresponding wing lug or projection on the cap, as described below. The wing groove 92 may also be provided with a mechanical stop that prevents further rotation of the wing within the wing groove similar to the locking lug groove. On the outside surface of the seat 26, a flange 21 and a recess 23 are formed in opposed locations in each of the sidewalls 79 as shown in FIGS. 8A and 8C. The flange 21 has an upper surface, lower surface and an outer surface.

Referring back to FIGS. 5A-5C, the closure mechanism 50 includes a cap 48 and set screw 52. The cap 48 incorporates at least one groove 112 and recess 113 for engagement with an inserter or driving tool to accomplish the partial rotation needed to lock the cap 48 into the seat 26. The inserter or driving tool may grip the cap for rotation, the recess provides room for "tangs" of the inserter tool, and the groove allows the "tangs" to clear the inner surfaces of the seat. A flange 116 may be provided which is an annular projection at the top surface. The flange 116 acts as a mechanical stop, to limit the amount of insertion of the cap into the seat. The outer surface of the cap includes at least one seat-engagement feature for engagement with the cap-receiving portion of the seat.

One seat-engagement feature on the cap is at least one locking lug 110 that is provided in at least one location around the circumference of the cap 48 and extending from the outer surface of the cap. As shown in FIGS. 5A and 5B, two locking lugs 110 are provided on or are integral with the flange 116 opposite from one another. The locking lugs 110 are sized for insertion into the rod channel 90. Also, the locking lugs 110 are configured to be rotatably inserted into the locking lug groove 88 in the seat 26. Typically, the locking lugs 110 are first inserted into the rod channel 90 and then rotated into position inside the locking lug groove 88.

Another seat-engagement feature on the cap is at least one wing 54 that is provided in at least one location around the circumference of the cap 48 extending outwardly from the outer surface of the cap. As shown in FIGS. 5A and 5B, two wings 54 are provided in opposed locations around the circumference of the cap 48. The two wings 54 are aligned with the two locking lugs 110 wherein the wings 54 are located below locking lugs 110. The wings 54 are sized for insertion into the rod channel 90. Also, the wings 54 are configured to be rotatably inserted into the wing groove 92. Generally, the cap 48 is placed into the seat 26 with the two wings 54 and the two locking lugs 110 in alignment with the rod channel 90 such that the cap 48 drops into the seat until the flange 116 abuts a surface of the locking lug groove 88. After the cap is seated, it is capable of being turned. Turning of the cap 48 rotates the wings 54 and the locking lugs 110 into the wing grooves 92 and locking lug grooves 88, respectively. To effect the rotation, a tool is used to engage the groove 112 and/or recess 113 of the cap to turn the cap 48 while it is inside the seat.

Figure 8D:
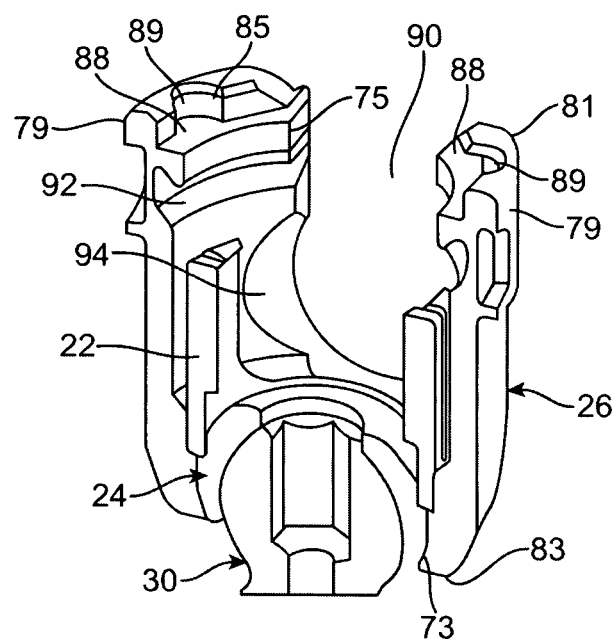
FIG. 8D illustrates a perspective, partial cross-sectional view of a screw system according to the present invention.

In one variation, as shown in the perspective close-up view of the seat 26 in FIGS. 8A and 8D, the cap (not shown) is turned until rotation is stopped by a wall 85 located in the locking lug groove 88 against which the locking lugs 110 abut. A second locking wall (not shown) may also formed in the opposite locking lug groove generally diagonally from wall 85. The degree of rotation is preferably approximately 90 degrees but the invention is not so limited and any degree of rotation is within the scope of the invention. The wall 85 serves as an anti-rotation mechanism that prevents the cap from turning past a locked position. Other anti-rotation mechanisms may also be employed.

In one variation, after the cap 48 is seated and rotated such that the wings 54 and locking lugs 110 are in the wing grooves 92 and locking lug grooves 88, respectively, a set screw 52 located inside the cap 48 is tightened. As the set screw 52 is tightened, the cap 48 rises relative to the seat 26, that is, the cap will move upwardly relative to the seat. This rise is arrested by the wings 54, also known as wing lugs, contacting the upper surface of the wing groove 92. In an alternative variation, the locking lugs alone or in conjunction with the wings are employed to arrest the rise of the cap as the set screw is advanced and a force, resulting from the set screw being biased against the seat, is applied to the rod below the set screw.

Furthermore, in one variation, counter-rotation of the cap 48 is prevented as the set screw 52 is advanced and the locking lugs 110 rise relative to the seat 26 into a recess 89 or window formed inside the locking lug groove 88 as shown in FIGS. 8B and 8D. The recess or window 89 includes a stop 91 against which the locking lugs 110 abut to prevent counter-rotation. The stop 91 is visible in FIG. 8B. After the cap 48 has moved upwardly upon set screw advancement such that the locking lugs 110 have substantially entered the recess or window 89, the locking lugs 110 are substantially moved out of the locking lug groove 88 and they cannot be moved back into the groove 88, and thus the cap cannot be removed, until the set screw is "backed off" and the cap drops or is "lowered" such that the locking lugs 110 reside again in the groove 88. It should be noted that a corresponding recess 89 and a corresponding wall 91 is formed in the other sidewall of the cap receiving portion of the seat 26.

The wing 54 has a reverse angle surface 114 (see FIG. 5B) to inhibit spreading of the seat. The wing lug groove 92 defined by the interior of seat 26 slidingly receives the wing lug 54 of the cap 48, and the cap is locked into the seat when the cap is rotated, for example, by 90 degrees. The reverse angle surface 114 keeps the seat 26 from splaying as the set screw 52 is rotated. In particular, as the set screw 52 rotation forces the cap upwards, the reverse angle surface 114 keeps the walls of the seat 26 from spreading outward. Otherwise, the forces of the cap upward movement would tend to spread the seat. In an alternative embodiment, the wings may snap into recesses of the wing lug groove 92 when an appropriate or predetermined degree of rotation has been achieved. Appropriate spring-loading may be employed to achieve this snapping feature.

As shown in FIGS. 5B and 5C, in one variation, the bottom surface of the set screw 52 includes a dome 118 that protrudes from the bottom surface of the set screw 52. As the set screw 52 is advanced, the feature 118 contacts the rod 40 and creates a single point, line or surface area of contact between the cap system 50 and the rod 40. This restrains less of the rod, allows some flexion and thus reduces the stiffness of the total device between the screws, leading to a better stress distribution throughout the construct, a lower stress concentration and enhanced fatigue performance. Examples of alternative features in the bottom surface of the set screw 52 include but are not limited to any one or more of the following used alone or in combination: a dome, nipple, aperture, raised surface, and a dome with an aperture.

Referring back to FIGS. 2A and 2B, the basic four set of components (retaining ring 22, coupler 24, seat 26, and screw 30), may be the same or similar for both the hinged assembly (first screw system) and the receiving cradle (second screw system) in a single or multi-level application as will be described in greater detail below. Generally, the coupler 24 snaps onto the screw head and with at least a portion of the screw 30 passed through the bore at the bottom end 83 of the seat 26, the coupler 24 and screw 30 are placed into the seat 26, and the retaining ring 22 is press-fitted in between the coupler 24 and seat 26 to complete the assembly. To this end, the seat 26 may have an internal tapered bore to hold the coupler and screw in a snug configuration. A pivoting rod 40 snaps into one of the first or second rod receiving portions 150, 152 of the retaining ring 22 and is pivoted such that at least a portion of the rod 40 extends through the rod channel 90 of the seat 26. In a multi-level application, a second pivoting rod 40 is snapped into one of the other of the first or second rod receiving portions 150, 152 and pivoted such that at least a portion of the rod 40 extends through the other side of the rod channel 90 of the seat. A closure mechanism is inserted into the opening at the first end 81 of the seat to close and retain one or two pivoting rods 40 inside the seat 26 and to lock the system into position. This process will be further described in greater detail below.

Figure 9A:
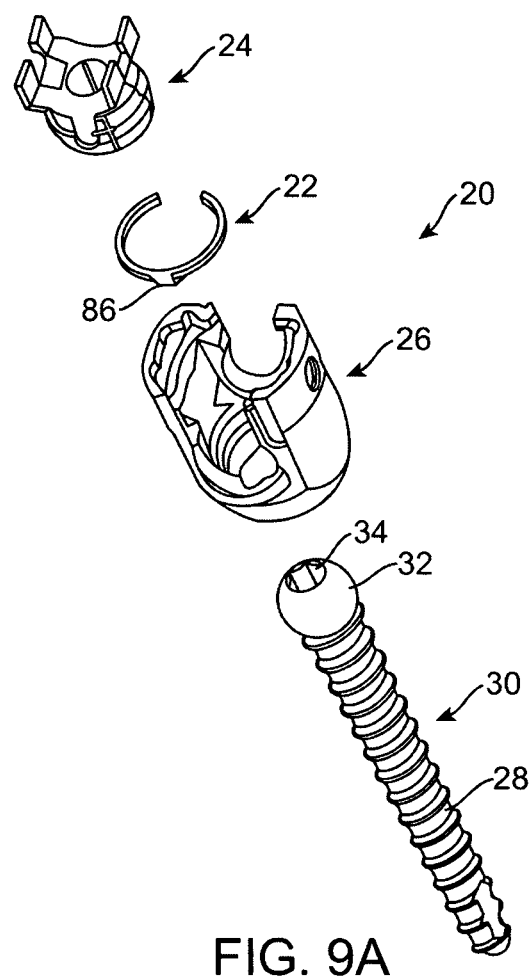
FIG. 9A illustrates a perspective view of an exploded screw system according to the present invention.

Turning now to FIG. 9A, there is shown an exploded perspective view of another variation of the present invention showing the screw 30, seat 26, coupler 24 and retaining ring 22 of the system 20 wherein the like reference numerals are used to reference like parts. The screw system 20 is shown having a screw 30 with threads 28. The threads 28 are appropriate for entering the bone of a patient. At a proximal end of screw 30 is a ball end 32. While a ball end 32 is shown, various other shapes may also be employed. A hex socket 34 that is interconnected with a guidewire lumen (not shown) extends through the general axial center of screw 30, and also can extend through the retaining ring 22, coupler 24 and seat 26. The system is suitable for being installed in a patient for treating at least one or more of the following: degenerative disc disease, spinal stenosis, spondylolisthesis, spinal deformities, fractures, pseudarthrosis, tumors, failed previous fusions, other vertebral segment trauma or diseases.

The ball end 32 of screw 30 is fitted into the bottom of the coupler 24, which has a spherical interior shape, as will be described in greater detail below. If end 32 has a different shape, the shape of the interior of the bottom of the coupler 24 may be similarly complimentary. No matter the shape, when the ball end is fitted into the bottom end of end of the coupler 24, the coupler 24 may be fitted into the "bucket-shaped" seat 26. Retaining ring 22 ensures that the coupler 24 does not escape from the interior of seat 26, and is pressed/snapped between the coupler 24 and seat 26 and described in greater detail below.

Figure 10A:
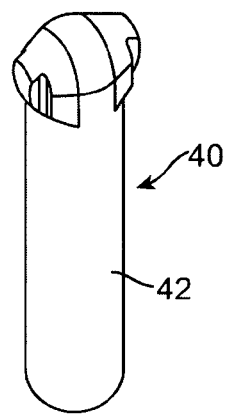
FIG. 10A illustrates a perspective view of a pivoting rod according to the present invention.
Figure 10B:
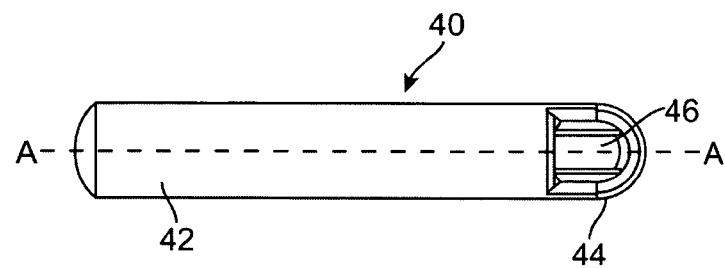
FIG. 10B illustrates a side view of a pivoting rod according to the present invention.
Figure 10C:
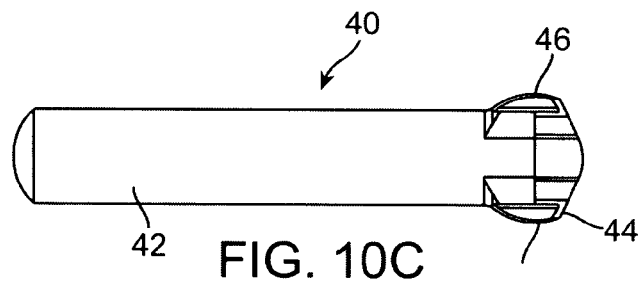
FIG. 10C illustrates a top view of a pivoting rod according to the present invention.
Figure 10D:
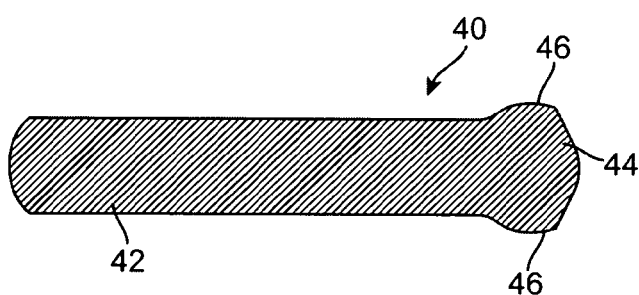
FIG. 10D illustrates a cross-sectional view along line A-A of FIG. 10B of a pivoting rod according to the present invention.
Figure 10E:
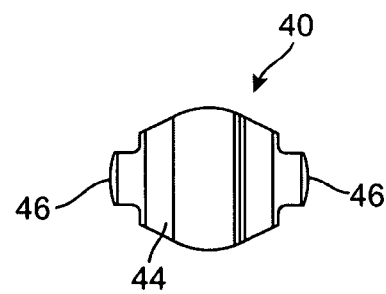
FIG. 10E illustrates an end view of a pivoting rod according to the present invention.
Figure 10F:
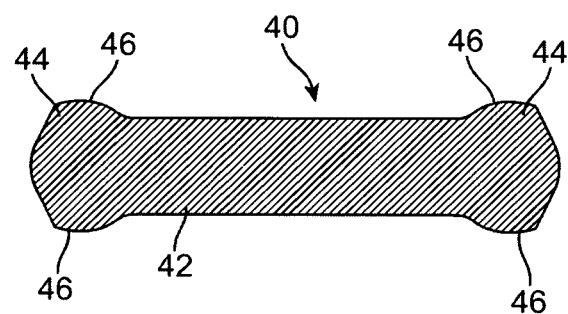
FIG. 10F illustrates a cross-sectional view of a pivoting rod according to the present invention.
Figure 20A:
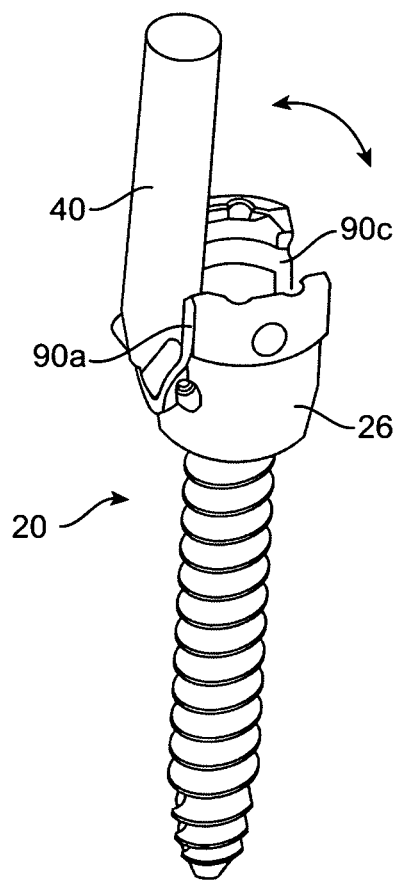
FIG. 20A illustrates a perspective view of a screw system with one pivoting rod connected to the screw system in a vertical orientation according to the present invention.
Figure 20B:
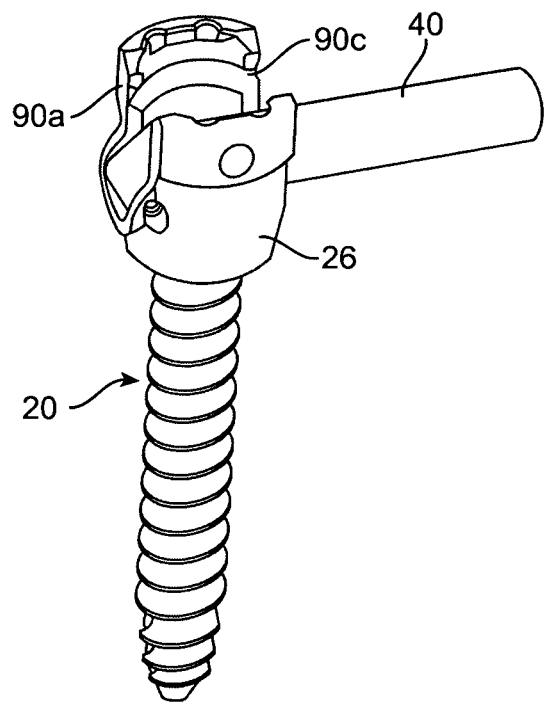
FIG. 20B illustrates a perspective view of a screw system with one pivoting rod connected to the screw system in a horizontal orientation according to the present invention.

FIGS. 10A-10F illustrate another variation of the rod 40 which is employed in the current variation of the present invention or in any of the other variations of the present invention. The rod 40 in FIGS. 10A-10F is shown to be straight. In another variation, a curved rod that conforms to the natural curve of the spine is employed. The pivoting rod 40 has a shaft 42, a connecting end 44, and at least two contacts 46 for connection with the seat 26 and, in particular, for connection with the coupler 24 of FIG. 9A or retaining ring 22 of FIG. 2A. The shaft 42 may vary in length, or may be adjustable by the physician, either by a telescoping mechanism or by being cut to measure. The end of the shaft 42 opposite that of connecting end 44 may be straight, as shown, or may itself incorporate a second connecting end 44 (as shown in FIG. 10F) or other type of end to enable trapping and capture in a seat of a screw system mounted to another spinal segment. The connecting end 44 may be approximately ball-shaped, square or rectangular solid, or other such shape, so long as the shape allows movement of the rod with respect to the seat 26 in at least one plane. In general, the rod 40 and the screw system 20 include mating features adapted to connect each other together. In particular, the retaining ring 22 of FIG. 2A or coupler 24 of FIG. 9A include mating features adapted to connect together. In another variation, the seat 26 includes mating features configured to connect the rod 40 to the screw system 20. One example of such a variation is shown in FIGS. 20*a* and 20*b*.

As shown in FIG. 10E, the contacts 46 of the connecting end are slightly curved. The curved surface may be substantially cylindrical, ellipsoidal or spherical shape such that a point or line contact is established in the connection such as, for example, with the coupler 24 of FIG. 9A or retaining ring of FIG. 2A. The curved contacts 46 assist in expanding the range of motion of the rod substantially within one or more planes creating a polyaxial rod. Furthermore, the contacts 46 provide for a point or surface area that is in contact with the retaining ring 22 or coupler 24 and thereby, create an advantageous snug-fit engagement. In one variation, the contacts 46 are flattened. In such a variation, the greater surface area of contact of the flattened sides 46 with the screw system 20 provides for a snug-fit engagement. The same closure mechanism 50 of FIGS. 5A-5C described above with respect to the screw system 20 is employed with the screw system 20 of FIG. 9A.

Various aspects of the seat, coupler, and retaining ring will now be discussed. Referring back to FIG. 9A, a retaining ring 22 is shown. The retaining ring 22 includes at least one projection 86, also known as a key, which engages features on the seat 26, to hold the retaining ring 22 and coupler 24 in place when assembled. The retaining ring 22 may include a split such that the retaining ring 22 is approximately C-shaped when viewed from above. One or more such splits may be formed. The retaining ring 22 snaps into place inside the seat 26 to secure the assembly.

Figure 11A:
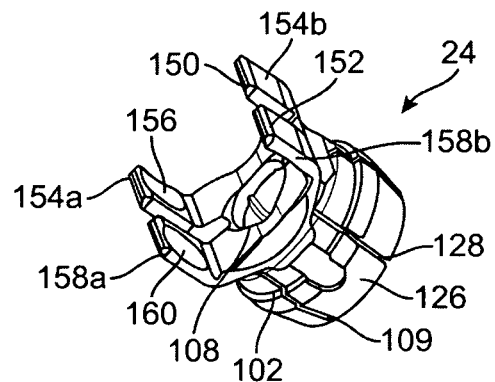
FIG. 11A illustrates a coupler according to the present invention.
Figure 11B:
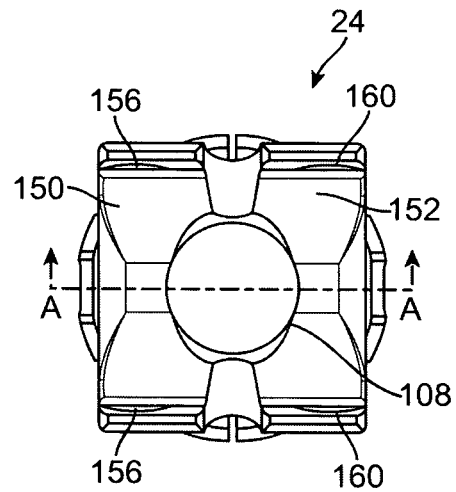
FIG. 11B illustrates a top view of a coupler according to the present invention.
Figure 11C:
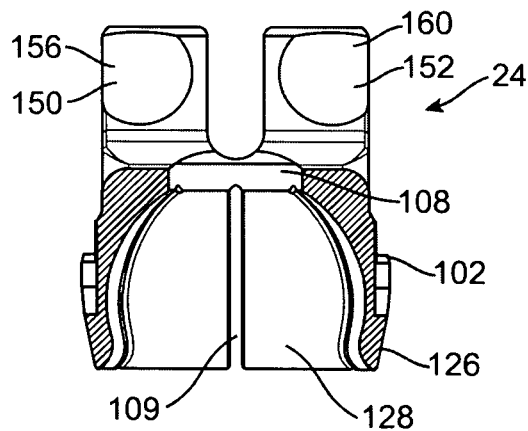
FIG. 11C illustrates a side cross-sectional view along line A-A of FIG. 11B of a coupler according to the present invention.

FIGS. 11A-11C show additional details of the coupler 24. The coupler 24 generally has a bone screw receiving portion 128. The bone screw receiving portion 128 is substantially domed shaped to correspond to the shape of the ball end 32 of the screw 30 received therein. A coupler access bore hole 108 provides access to the engagement means of the screw such as a hex socket.

Still referencing FIGS. 11A-11C, the coupler 24 includes at least one rod receiving portion 150. The variation in FIGS. 11A-11C includes two rod receiving portions: a first rod receiving portion 150 and a second rod receiving portion 152 adjacent to each other. Each of the first and second rod receiving portions 150, 152 are a pair of upstanding forks extending from a substantially annular base that may or may not include one or more splits described above. The first rod receiving portion 150 includes a pair of upstanding prongs 154*a*, 154*b* which together are configured to retain a first rod. The first rod receiving portion 150 is configured to retain the first rod in a press-fit, friction fit, slot and pin engagement or any other suitable engagement means that permits the rod to rotate, pivot or otherwise move in at least one plane while retained within the first rod receiving portion 150. In one variation, each prong 154a, 154b includes a concave region 156 or undercut that helps to retain the rod in place. The concave region 156 is substantially complementary to the shape of the connecting end 44 of the rod 40. A convexly shaped connecting end 44 is retained and swivels easily for polyaxial motion when retained inside a concavely shaped prong. Similar to the first rod receiving portion 150, the second rod receiving portion 152 includes a pair of upstanding prongs 158a, 158b which together are configured to retain a second rod. The second rod receiving portion 152 is configured to retain the second rod in a press-fit, friction fit, slot and pin engagement or any other suitable engagement means that permits the rod to rotate, pivot or otherwise move in at least one plane while retained within the first rod receiving portion. In one variation, each prong 158a, 158b includes a concave region 160 or undercut that helps to retain the rod in place. The prongs are allowed to flex slightly to retain the rods and allow them to move in at least one plane while connected. The coupler 24 is configured to receive and retain securely two rods, side-by-side, within one seat 26 for a multi-level application in which at least three vertebrae are interconnected. The coupler 24 that is configured to receive two pivoting rods may also be employed to receive one pivoting rod in a single level application. In such an application, the pivoting rod is pivoted away from the adjacent rod channel 90a (see FIG. 19A) in the seat 26a and towards the opposite rod channel 90b (see FIG. 19A) in the same seat 26a as will be described in greater detail below with respect to FIG. 19A.

Still referencing FIGS. 11A-11C, a lip 102 is provided on the coupler 24 to mate with the retaining ring 22. An approximately spherical bore 128 or screw head receiving portion is provided in the interior of the bottom of the coupler 24 that "snap-fits" over the head 32 of the screw 30 to allow a limited amount of rotation, for example 60 degrees of polyaxial rotation. Hence, the screw system 20 of the present invention provides for both a polyaxial screw and polyaxial rod in the same construct. The exterior surface of the coupler 24, exterior of the spherical bore 128, may be a generally tapered ramp 126 (FIGS. 11A and 11C). At least one slit 109 is provided to allow circumferential compression around the screw head 32.

Figure 12A:
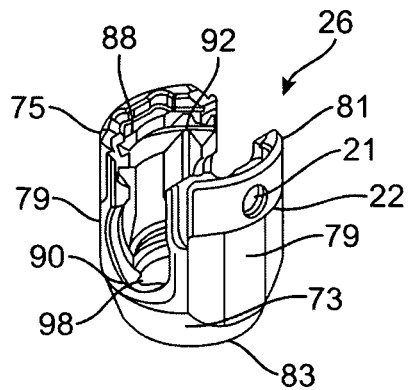
FIG. 12A illustrates a perspective view of a seat according to the present invention.
Figure 12B:
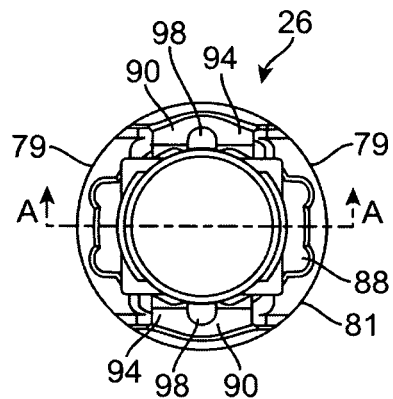
FIG. 12B illustrates a top view of a seat according to the present invention.
Figure 12C:
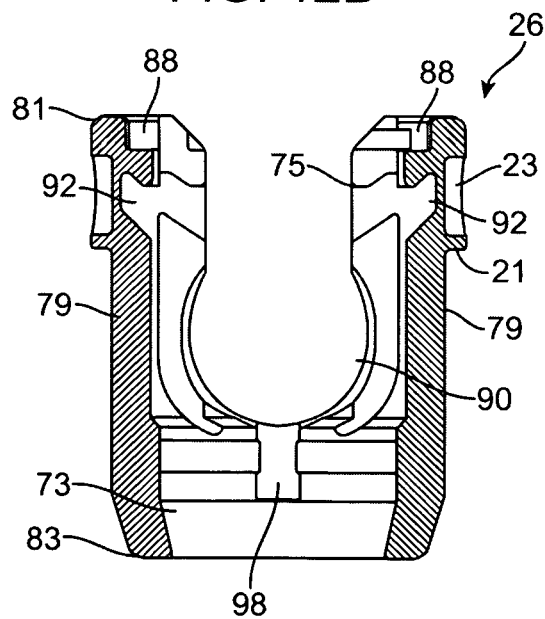
FIG. 12C illustrates a side cross-sectional view along line A-A of FIG. 12B of a seat according to the present invention.

Referring now to FIGS. 12A-12C, the seat 26 includes an inner surface and an outer surface and a first end 81 and a second end 83. At least one sidewall 79 extends between the first end 81 and the second end 83 forming a top opening at the first end 81 and at least one "U"-shaped void or rod channel 90 into which the rod may pivot when installed. Two rod channels 90 or voids are shown in FIGS. 12A-12C in which voids 90 are defined in part by seat rod channel bevels 94. The rod channels 90 are curved or rounded to permit the polyaxial movement of the pivoting rod 40 when installed. A void or keyway 98 is provided near the base of the seat to engage each projection 86 to orient the retaining ring 22 in a press-fit fashion with respect to the coupler 24 and seat 26. In FIG. 12B, the keyways 98 are adjacent the rod channel bevels 94. The seat rod channel bevels may generally match bevels formed in the coupler in shape, pitch, angle, slope, etc., and assist in orienting the rod pivot arc as well as orienting the rod channel to receive the rod.

The seat 26 includes a closure mechanism receiving portion 75 or a cap receiving portion 75 configured to receive a cap 48 at the first end 81 and a coupler receiving portion 73 configured to receive a coupler 24. The coupler receiving portion 73 includes a tapered ramp that corresponds to a tapered ramp on the coupler 24. The cap receiving portion 75 includes a locking lug groove 88 that is provided near the top of the seat 26 to slidingly receive a corresponding locking lug or projection of the cap, described below. Cap rotation of, for example 90 degrees, secures the cap in place. The locking lug groove 88 may further include an anti-rotation mechanism, such as a mechanical stop. In this way, the locking lugs may be fixed in the amount of rotation needed to secure them in place. A wing groove 92 is also provided on the seat 26 in both of the sidewalls 79, to slidingly receive and engage a corresponding wing lug or projection on the cap, as described below. The wing groove 92 may also be provided with a mechanical stop that prevents further rotation of the wing within the wing groove similar to the locking lug groove. On the outside surface of the seat 26, a flange 21 and a recess 23 are formed in opposed locations in each of the sidewalls 79 as shown in FIGS. 12A and 12C. The flange 21 has an upper surface, lower surface and an outer surface. The closure mechanism 50 includes a cap 48 and set screw 52 which engages the seat 26 as described above with respect to FIGS. 5A-5C.

Figure 13:
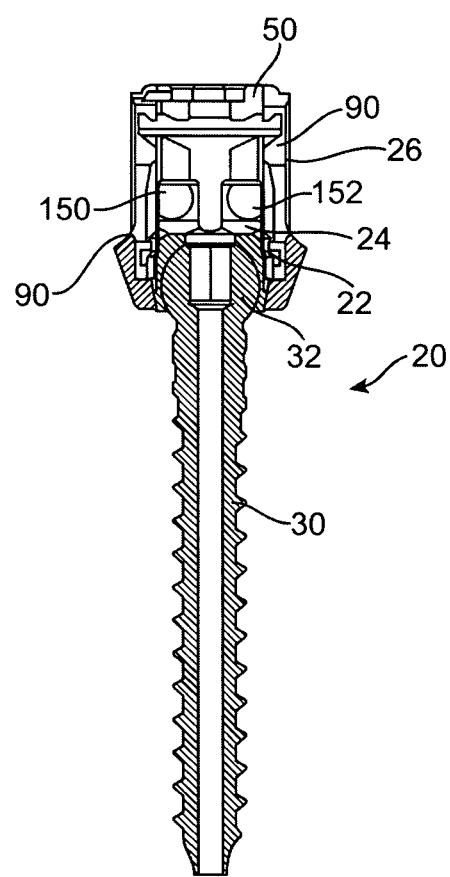
FIG. 13 illustrates a side cross-sectional view of a screw system according to the present invention.

Referring back to FIG. 9A, the basic four set of components (retaining ring 22, coupler 24, seat 26, and screw 30), may be the same or similar for both the first screw system to which the first end of the rod is connected and the second screw system in which the second end of the rod is received or pivoted into in a single or multi-level application. Generally, the coupler 24 snaps onto the screw head with at least a portion of the screw 30 passed through the bore at the bottom end 83 of the seat 26, the coupler 24 and screw 30 are placed into the seat 26, and the retaining ring 22 is press-fitted in between the coupler 24 and seat 26 to complete the assembly. To this end, the seat 26 may have an internal tapered bore to hold the coupler and screw in a snug configuration. An assembled screw system 20 without a rod 40 is shown in cross-section in FIG. 13. Prior to insertion of the closure mechanism 50, a pivoting rod 40 snaps into one of the first or second rod receiving portions 150, 152 of the coupler 24 and pivoted with respect to the coupler 24 such that at least a portion of the rod 40 extends through the rod channel 90 of the seat 26. In a multi-level application, a second pivoting rod 40 is snapped into one of the other of the first or second rod receiving portions 150, 152 and pivoted with respect to the coupler 24 such that at least a portion of the rod 40 extends through the other side of the rod channel 90 of the seat. A closure mechanism 50 is inserted into the opening at the first end 81 of the seat 26 to close and retain one or two pivoting rods 40 inside the seat 26 and to lock the system into position. This process will be further described in greater detail below.

Figure 14G:
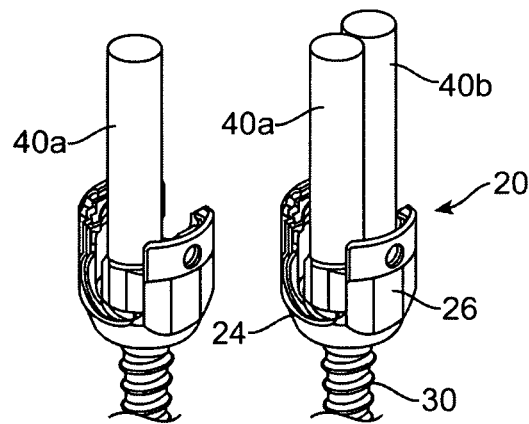
FIG. 14G illustrates a partial perspective view of a screw system with one pivoting rod and a screw system with two pivoting rods connected to the screw system according to the invention.

FIGS. 14A-14G illustrate a method of rod installation and cap and set screw fixation. Any of the embodiments for the screw system 20 described above may be employed with the methods described hereinbelow. Firstly, referring to FIG. 14A, with a bone screw system 20 implanted into a first vertebra (not shown) of a patient's spine, a first rod 40a is provided and delivered to the operative site in an open, mini-open, percutaneous or minimally-invasive method employing instrumentation and methods such as that described in U.S. Patent Publication No. 2007/0043359 published on Feb. 22, 2007 and in U.S. Patent Publication No. 2007/0239159 published on Oct. 11, 2007 both of which are incorporated herein by reference in their entireties. The instrumentation, including a cannula, used to deliver the rod(s) 40a is not shown in FIGS. 14A-14F. As shown in FIG. 14A, the first rod 40a is delivered such that the connecting end 44 or first end 200 of the rod 40a leads. Although, the first rod 40a is shown to be straight with one connecting end 44a, the rod 40a may be curved, bent and/or include a second connecting end at the other end of the rod 40*a*. In FIG. 14B, a first rod 40*a* is disposed in the seat 26 and connected to the first rod receiving portion 150 of the screw system 20. In FIG. 14C, a second rod 40*b* is provided and delivered to the operative site also in an open, mini-open, percutaneous or minimally-invasive method as the first rod 40*a* with the connecting end 44*b* or first end 202 of the second rod 40*b* leading insertion. Although, the second rod 40*b* is shown to be straight with one connecting end 44, the rod 40*b* may be curved, bent and/or include a second connecting end at the other end of the rod 40*b*. In FIG. 14D, the second rod 40*b* is disposed in the seat 26 and connected to the second rod receiving portion 152 of the screw system 20. Also, in FIG. 14D, the first rod 40*a* is shown pivoted with respect to the seat 26 approximately 90 degrees from a generally vertical orientation with respect to the screw system 20 to a generally horizontal orientation such that a second end 204 of the first rod 40*a* extends away from the seat 26. The second rod 40*b* in FIG. 14D is shown in a generally vertical or insertion orientation with respect to the seat 26; whereas, the first rod 40*a* is shown in a second orientation such that the second end 204 is received in a seat, receiving cradle or rod receiving portion of a similar or exact type of screw system 20 implanted in a second vertebra such as an adjacent vertebra of the patient (not shown). FIG. 14E shows the second rod 40*b* pivoted with respect to the seat 26 approximately 90 degrees from a vertical or first insertion orientation such that a second end 206 of the second rod 40*b* is received in a seat, receiving cradle or rod receiving portion of a similar or exact type of screw system 20 implanted in an third vertebra such as an adjacent vertebra of the patient (not shown). FIG. 14E also illustrates a closure mechanism 50 introduced and connected to the seat 26 in FIG. 14F. Whereas in FIGS. 14A-14F, the first and second rods 40*a*, 40*b* are loaded into the seat 26 individually, the first and second rods 40*a*, 40*b* may also be loaded simultaneously or pre-loaded with the screw system 20 and delivered together with the screw system 20 in a connected fashion.

Figure 15A:
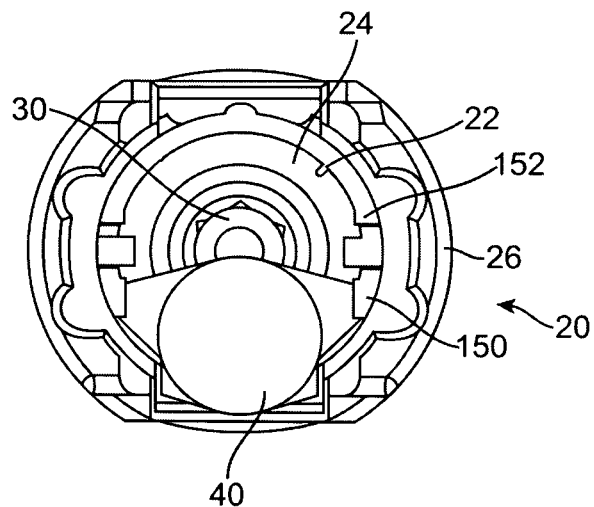
FIG. 15A illustrates a top view of a screw system and a pivoting rod connected to the screw system according to the present invention.
Figure 15B:
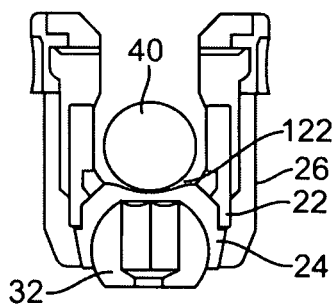
FIG. 15B illustrates a side cross-sectional view of a screw system and pivoting rod according to the present invention.
Figure 15C:
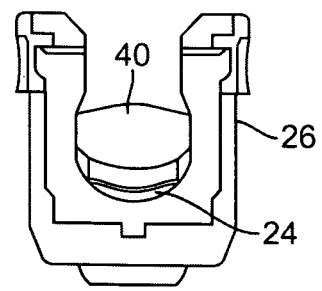
FIG. 15C illustrates a side view of a screw system and pivoting rod according to the present invention.

Turning now to FIG. 15A, there is shown a top view of a rod 40 disposed inside a rod receiving portion 150 in a screw system 20 of the type described in FIGS. 2-8. However, the top view would be substantially similar for screw system 20 of FIGS. 9-13. In the variation of FIGS. 2-8, the rod receiving portion 122 of the coupler 24 substantially conforms to the shape of the rod 40 as shown in FIG. 15B where a curved rod receiving portion 122 of the coupler 24 conforms to a curved rod 40. A substantially V-shaped rod-receiving portion 122 configured to support a substantially V-shaped rod 40 is shown in FIG. 15C.

It should be noted that FIGS. 14A-14F illustrate insertion of the rod 40 in a vertical orientation that is substantially parallel to the orientation of the seat 26 to minimize the opening, incision or pathway into the patient in a minimally invasive, percutaneous or mini-open procedure. According to one variation of the invention, the rod 40 may be oriented 90 degrees with respect to the seat longitudinal axis such that it is substantially perpendicular to the longitudinal axis of the seat and be capable of insertion into and connection with the seat. In another method of practicing the invention, the rod 40 can be oriented at any angle relative to the longitudinal axis of the seat for insertion and connection into the seat. The screw system 20 allows for the bone screw 30 to be first set into the bone and then, following the insertion of the bone screw, the rod is attached in any of the various orientations of the rod relative to the seat just discussed. This two step process is advantageous in the event that patient anatomy makes it difficult to insert the rod-plus-screw system combination at the same time. A single step process in which the rod-plus-screw system combination is inserted at the same time is advantageous in expediting the entire procedure. The system is versatile such that at least one rod may be attached first to the seat in the various orientations of the rod relative to the screw just described and then the entire system 20 (the rod-plus-screw system combination) set into the bone simultaneously using instrumentation that grips the seat 26 at the flange 21 and/or recesses 23, for example, or the rod(s) 40 itself. After the rod is attached, the closure mechanism 50 is seated and locked. Prior to the locked configuration, that is a complete tightening of the set screw, and with or without the closure mechanism 50 in position, the system retains two levels of freedom of motion. Firstly, the rod is free to be adjusted with respect to the seat and secondly, the seat is free to be adjusted relative to the screw. Hence, both the rod and the screw retain a degree of motion relative to seat, with or without the cap in place, which allows the clinician to custom orientate the seat with respect to the bone screw as well as with respect to the rod. The freedom of motion of each of the at least one rod with respect to the seat and of the screw with respect to the seat is generally in at least one plane or otherwise polyaxial. The freedom of motion also permits the clinician to custom orientate the rod with respect to the seat with the system deployed inside the patient and in the unlocked configuration. This freedom of motion advantageously provides the surgeon with a much needed, increased ease of implantation.

With the cap in the cap-receiving portion of the seat and as the set screw is advanced within the cap, the screw contacts the rod and the cap rises relative to the seat until the wing lugs contact the upper surface of the wing lug groove and the cap is thereby biased into a locked configuration by the seat. Further advancement of the set screw exerts additional force onto the rod and it is transferred to the coupler and drives the coupler downward. As the set screw drives the coupler retainer downward, e.g., through a force transmitted through the rod, the coupler is pushed downward, further into the seat. The tapered ramp of the coupler engages the corresponding tapered ramp in the seat. The coupler is radially compressed (which is possible because of the slits 109), thus gripping the screw head securely and simultaneously locking movement of the bone screw and the rod into a desired position. In one variation, the lockdown of the bone screw does not occur simultaneously with the lockdown of the rod but are locked independently. For example, if the rod embodiment of FIG. 4B is employed, advancement of the set screw contacts the ball portion 41 that slides and rotates with respect to the rod 40. The contact with the set screw transmits force directly to the coupler to effect the lockdown of movement of the bone screw relative to the seat without locking movement of the rod relative to the seat, thereby, allowing the rod to slide and rotate with respect to the ball portion 41. Further advancement of the set screw compresses the ball portion 41 locking the rod into position relative to the ball portion 41 after the bone screw has been locked. In an alternative variation, the advancement of the set screw contacts the ball portion 41 and compresses the ball portion 41 to effect arrest movement of the rod with respect to the seat without locking down movement of the bone screw relative to the seat. Further advancement of the set screw transmits force to the coupler to effect lockdown of the bone screw relative to the seat after the rod has been locked first. This independent lockdown mechanism permits the selective lockdown of the rod relative to the seat and bone screw relative to the seat.

With the closure mechanism 50 in place on the seat, different variations of the invention provide two or more of the following configurations: an unlocked configuration, a partially locked configuration and a fully locked configuration.

In the unlocked configuration, both the rod and screw move relative to the seat. In the partially locked configuration, one of the rod and screw moves relative to the seat and movement of the other is arrested. In a fully locked configuration, movement of both the rod and screw is arrested with respect to the seat. Variations of the invention include configurations that permit the system to go reversibly from an unlocked configuration to a fully locked configuration, or reversibly from an unlocked configuration to a partially locked configuration, or reversibly from an unlocked configuration to a partially locked configuration to a fully locked configuration. In one variation, the fully locked configuration permits some limited movement of the rod and screw relative to the seat but said movement is much reduced relative to the unlocked configuration. In another variation, the partially locked configuration permits some limited movement of one of the rod and screw relative to the seat but said movement is much reduced relative to the unlocked configuration.

Figure 16A:
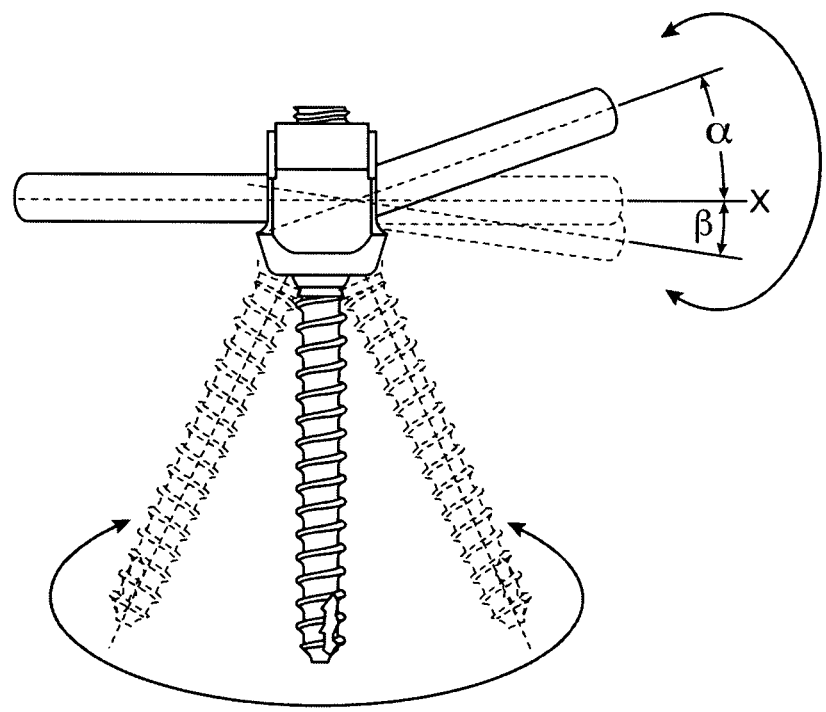
FIG. 16A illustrates a side view of two pivoting rods connected to a screw system showing the degree of angulation of one of the pivoting rods in a vertical plane according to the present invention.
Figure 16B:
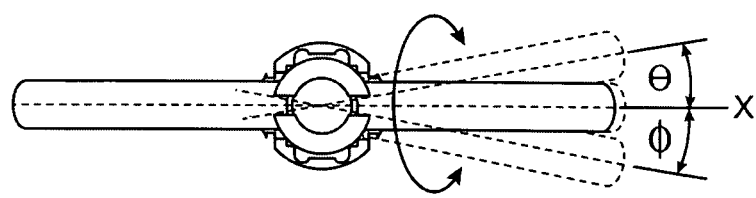
FIG. 16B illustrates a top view of two pivoting rods connected to a screw system showing the degree of angulation of one of the pivoting rods in a horizontal plane according to the present invention.

It is noted that with the closure mechanism positioned in the seat, the rod is not in vertical orientation or parallel to the longitudinal axis of the seat such that the rod extends through the top opening of the seat, but instead, at least a portion of the rod extends through the rod channel 90. However, the rod still retains a range of motion while disposed in the rod channel and in the unlocked or partially locked configurations in which the rod movement with respect to the seat is not arrested. FIGS. 16A and 16B illustrate the approximate polyaxial range of motion of the rod in at least one plane. The rod moves polyaxially with respect to the seat. In another variation, the rod moves polyaxially in a range of motion as required by the anatomy. In another variation as FIG. 16A illustrates, the range of motion of the polyaxial rod in a vertical plane where the angle a is approximately 0 to 45 degrees and preferably 0 to approximately 25 degrees of travel upwardly from the horizontal position X and where the angle β is approximately 0 to 45 degrees, preferably 0 to 25 degrees, and in another variation preferably 0 to approximately 8 degrees of travel downwardly from the horizontal position X as shown in FIG. 16A. FIG. 16B illustrates the range of motion of the polyaxial rod in one variation. In another variation, the range of motion is in a horizontal plane as required by patient anatomy. In another variation, the rod moves polyaxially with respect to the seat. In another variation, the range of motion in the horizontal plane as shown in FIG. 16B is such that θ and φ each are approximately 0 to approximately 20 degrees and preferably 0 to approximately 12 degrees of travel in each direction from the nominal X position as shown in FIG. 16B. It is noted that the rod is permitted to angulate within the range thus specified. There may even be additional structural elements employed to permit some degree of motion while in the locked configuration. Some examples of such elements include, a reduced point of contact with the set screw as described herein, flexible prongs in the rod receiving portions and shock absorption elements deployed between the coupler and the seat for example. Hence, the term "locked" is used to describe the restriction of motion of the rod and/or screw relative to the unlocked configuration. Also, the term "locked" is used with respect to the cap to describe the cap being seated inside the seat whether or not the movement of the rod and/or screw is arrested.

Figure 17A:
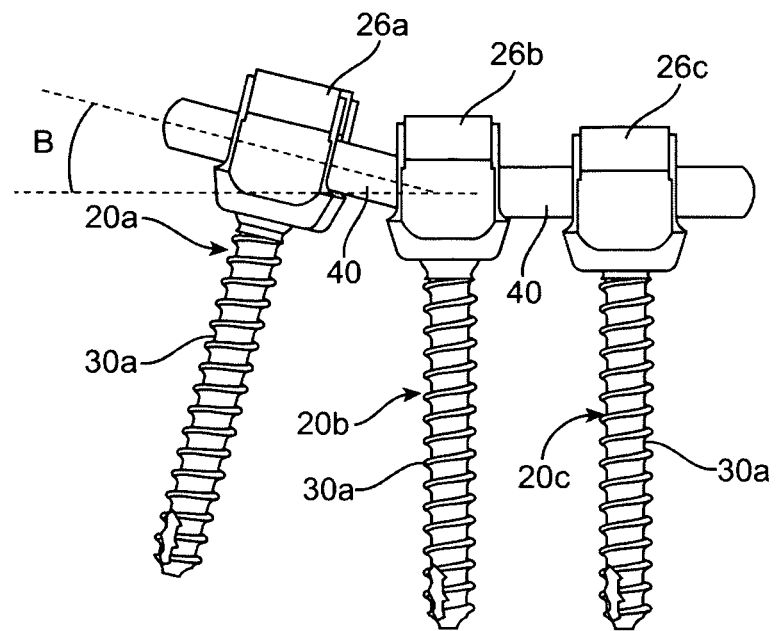
FIG. 17A illustrates a side view of three screw systems interconnected by two pivoting rods according to the present invention.
Figure 17B:
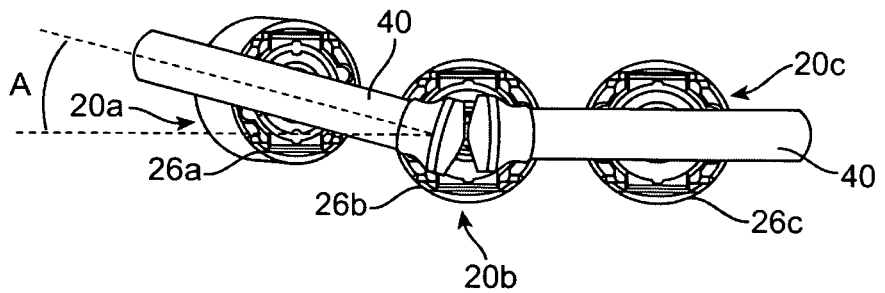
FIG. 17B illustrates a top view of three screw systems interconnected by two pivoting rods according to the present invention.

Polyaxial angulation of the rod is particularly advantageous in cases of difficult patient anatomy as the novel construct of the present invention allows single and multi-level installations as shown in FIGS. 17A and 17B wherein one or more of the screw system implantations 20a, 20b, 20c result in at least one of the seats 26a being vertically and/or horizontally displaced relative to at least one of the other screw systems such that one or more of the seats is not aligned with one or more of the other seats as shown in FIGS. 17A and 17B. FIG. 17A provides a side view of a first screw system 20a implanted in a first vertebra (not shown) at an angle B in a first plane with respect to the other two screw systems. FIG. 17B provides a top view illustrating the first screw system 20a displaced at an angle A in a second plane with respect to screw systems 20b and 20c. Closure mechanisms are not shown in FIG. 17B. As shown in FIGS. 17A and 17B, screw systems 20a, 20b, 20c do not have to be in line for the system to work. For the same situation as illustrated in FIGS. 17A and 17B, prior art systems employ a single long rod that spans all three screw systems 20a, 20b, 20c and hence, would not be able to adapt to the angulations shown. As a result, prior art systems burden the surgeon with the need to align and position the screws to allow the rod to be seated. In complex patient anatomies, the present invention with one or more rods placed at angled orientations mimic the natural lordosis of the spine and alleviates difficulties for the surgeon making for an easier and quicker installation and potentially one with less adverse long term effects facilitating fusion.

Figure 18:
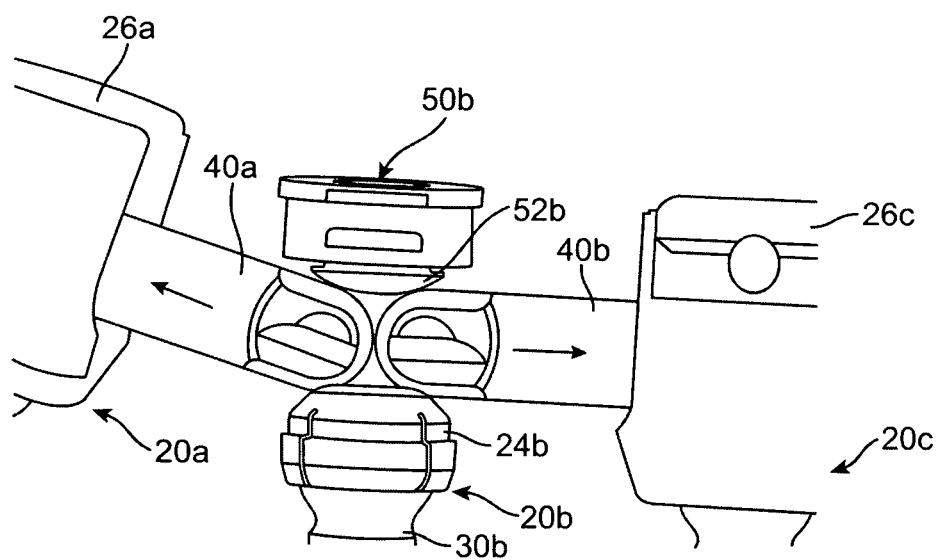
FIG. 18 illustrates a side partial view of three screw systems interconnected by two pivoting rods according to the present invention.

Turning now to FIG. 18, two seats 26a, 26c are shown in a multi-level installation of three bone screw systems 20a, 20b, 20c interconnected by two rods 40a, 40b according to the present invention. The seat of the middle bone screw system 20b is not shown for clarity in order to illustrate the interaction of the rods 40a, 40b, coupler 24b, screw 30b and closure mechanism 50b of the middle system 20b. When the middle system 20b is capped with the closure mechanism 50b, the set screw 52b is advanced to contact the rods 40a, 40b which transmits force to the coupler 24b which has a taper that matches the taper on the seat (not shown) that assist in compressing the coupler 24b to lock down the polyaxial motion of the screw 30b. The configuration of the set screw 52b and rods 40a, 40b results in the rods moving slightly outwardly as shown by the arrows as the set screw is advanced 52b after-which the adjacent seats 26a and 26c are locked. Alternatively this outward motion of the rods 40a, 40b is prevent by the adjacent seats 26a, 26c, respectively, in the event they are locked down first.

Figure 19A:
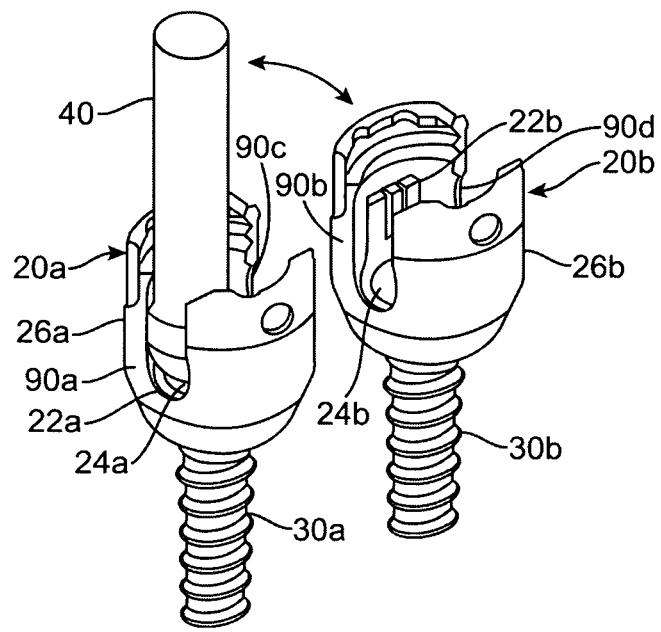
FIG. 19A illustrates a perspective view of two screw systems with one pivoting rod seated in one of the screw systems according to the present invention.
Figure 19B:
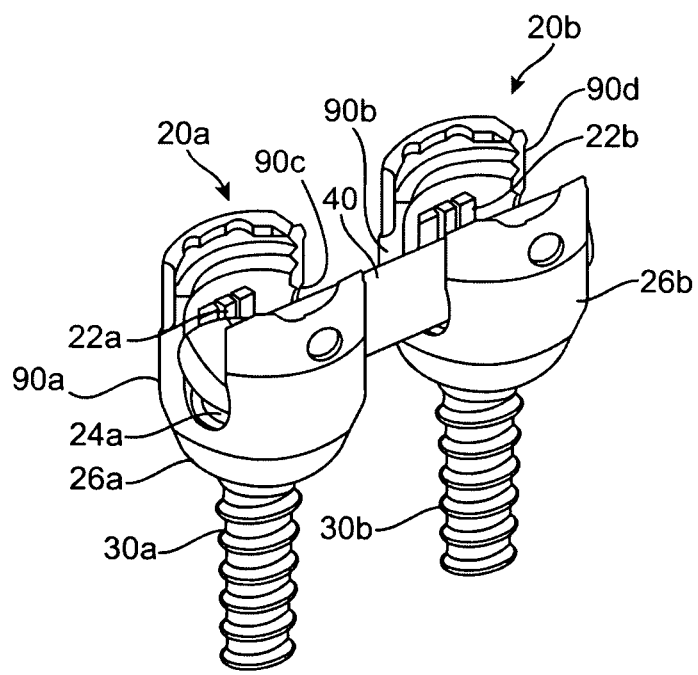
FIG. 19B illustrates a perspective view of two screw systems with one pivoting rod seated in both of the screw systems according to the present invention.

Turning now to FIGS. 19A and 19B, two adjacent bone screw systems 20a, 20b of the present invention are shown in a single level application in which the two bone screw systems 20a, 20b are implanted in two vertebrae (not shown), respectively, along the same side of the patient's spine. Screw systems implanted along the other side of the patient's spine are not shown. Each of the bone screw systems 20a, 20b includes a seat 26a, 26b, coupler 24a, 24b, retaining ring 22a, 22b and bone screw 30a, 30b, respectively. The closure mechanisms are not shown in FIGS. 19A and 19B and although the screw system variation of FIG. 2 is shown, any screw system such as the variation of FIG. 9 may also be employed. A single rod 40 is employed in the single level application to connect the constructs and thereby assist fusion and connect the two vertebrae together. The retaining ring 22 described above with respect to FIGS. 2-8 that is configured to receive two pivoting rods may also be employed to receive one pivoting rod in a single level application as shown in FIGS. 19A, 19B. In such an application, the rod 40 is inserted into the rod receiving portion of seat 26a that is located distally from the adjacent seat 26b and pivoted away from the rod channel 90a in the seat 26a that is adjacent to the rod receiving portion and pivoted towards the opposite rod channel 90c in the same seat 26a as generally shown by the arrow in FIG. 19A. The pivoting rod 40 moves from a substantially vertical orientation or substantially parallel to the opening or longitudinal axis of the seat 26a to a substantially horizontal or substantially perpendicular to the opening of longitudinal axis in the seat 26*a*. As shown in FIG. 19B, the rod 40 pivots into the adjacent seat 26*b* extending through rod channels 90*c* and 90*b* and in one variation, extending additionally through rod channel 90*d* as shown in FIG. 19B. Although the embodiment of FIGS. 2-8 is shown in FIGS. 19*a*, 19*b*, the embodiment of FIGS. 9-13 may also be employed in a single level application of the present invention in which two vertebrae are interconnected by the pivoting rod 40. Hence, the coupler 24 of FIGS. 9-13 that is configured to receive two rods may also be employed to receive one pivoting rod in a single level application to interconnect two vertebral bodies. An alternative variation of the bone screw system is shown in FIGS. 20A and 20B in which the rod 40 is configured for attachment to the seat 26 and reversibly pivotable (in the direction of the arrow) towards the opposite rod channel 90*c* and into an adjacent seat (not shown) implanted in another vertebra (not shown). The rod attachment is shown to be a pinned connection to the seat 26. Other connections of the rod to the seat known to one having ordinary skill in the art are within the scope of the present invention. The configuration of FIGS. 20A and 20B while shown for a single level application may be adapted for a multi-level application in which two rods are connectable to the seat in a similar fashion with each rod pivoting outwardly in opposite directions to interconnect three vertebral bodies.

Figure 21:
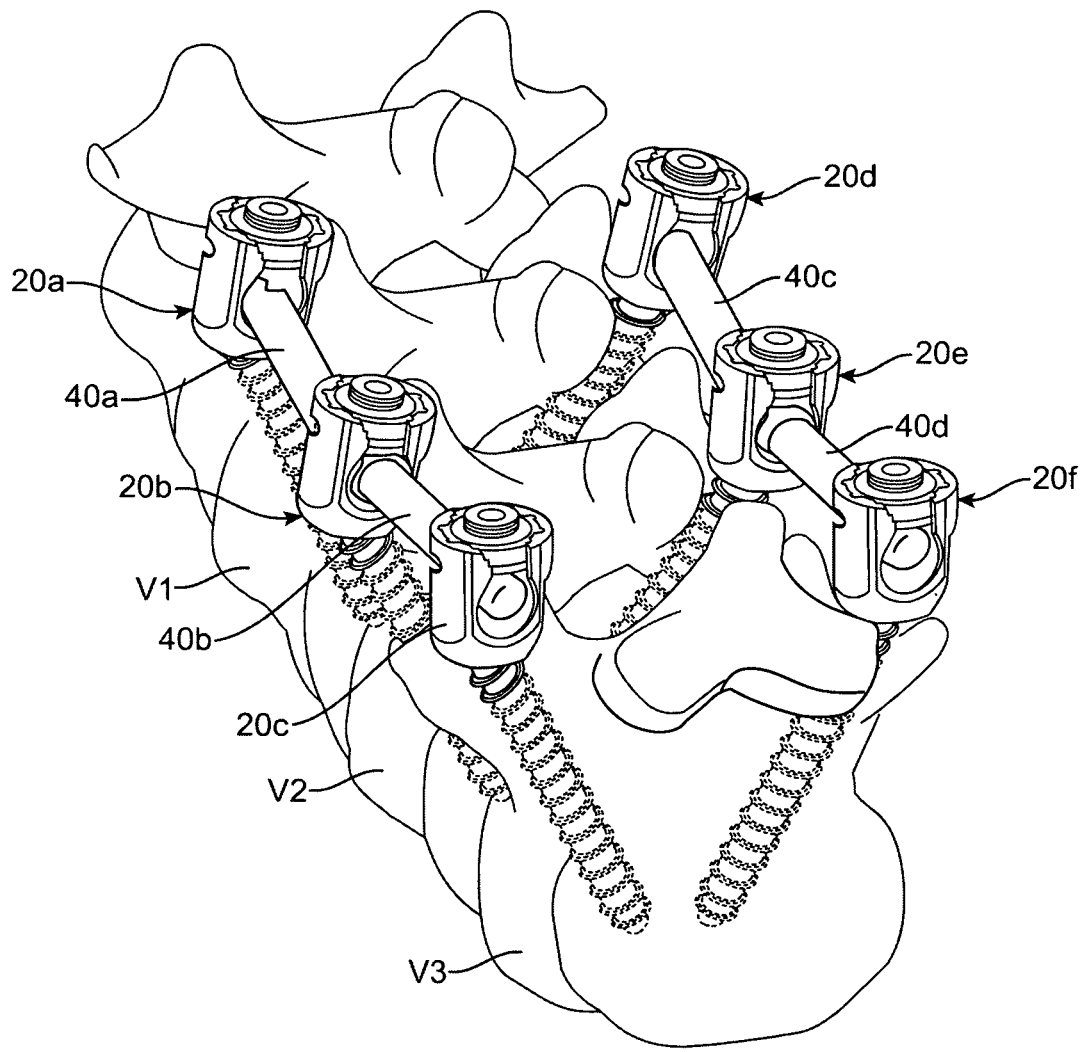
FIG. 21 illustrates a perspective view of six screw systems and four pivoting rods implanted in a segment of a human spine according to the present invention.
Figure 22A:
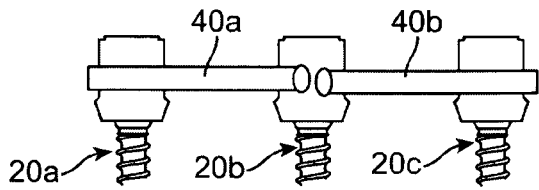
FIGS. 22A-22G illustrate three screw systems interconnected with two pivoting rods according to the present invention.
Figure 22B:
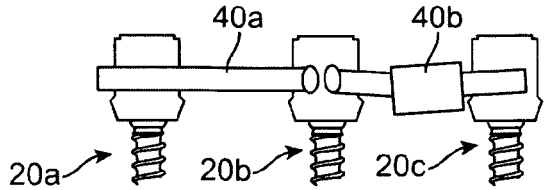
Figure 22C:
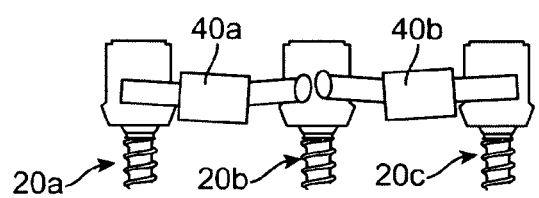
Figure 22D:
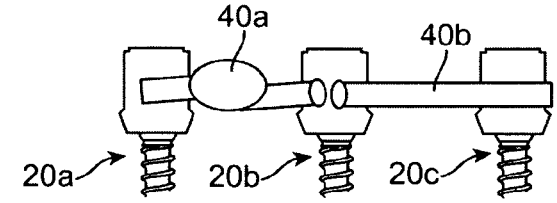
Figure 22E:
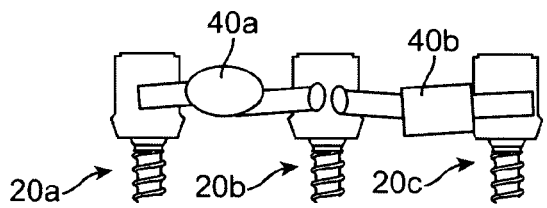
Figure 22F:
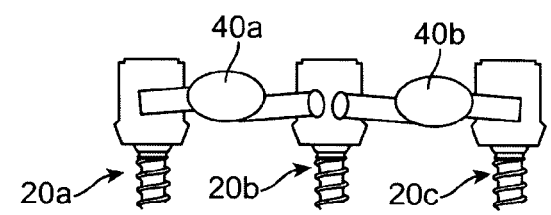
Figure 22G:
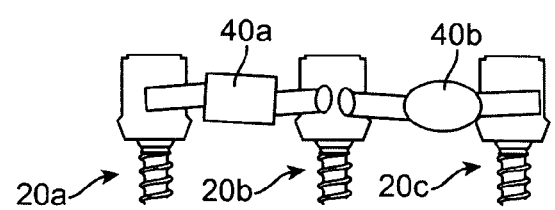

Turning now to FIG. 21, there is shown a typical installation environment of the bone screw systems 20 of the present invention in a multi-level application joining three vertebrae together. In particular, systems 20*a*, 20*b* and 20*c* are implanted along one side of a patient's spine into vertebrae V1, V2 and V3, respectively. And, systems 20*d*, 20*e* and 20*f* are implanted along the other side of a patient's spine in vertebrae V1, V2 and V3, respectively. Rod 40*a* is delivered and inserted into system 20*b* and pivoted into system 20*a* to interconnect vertebrae V1 and V2. Rod 40*b* is delivered and inserted into system 20*b* and pivoted to be seated into system 20*c* to interconnect vertebrae V2 and V3. Rod 40*c* is delivered and inserted into system 20*e* and pivoted into system 20*d* to interconnect vertebrae V1 and V2. Rod 40*d* is delivered and inserted into system 20*e* and pivoted to be seated into system 20*c* to interconnect vertebrae V2 and V3. More than three vertebrae may be interconnected with implantation of additional systems.

Still referencing FIG. 21, the rods 40*a*, 40*b* installed in bone screw systems 20*a*, 20*b*, 20*c* and rods 40*c*, 40*d* installed in bone screw systems 20*d*, 20*e*, 20*f* are shown to be substantially straight; however, one or more bent or slightly curved rods may also be employed entirely or in any combination with one or more straight rods in the multi-level installation shown in FIG. 21. Further combinations wherein one or more of the rods 40*a*, 40*b*, 40*c* and 40*d* is a dynamic or semi-rigid rod are within the scope of the present invention. In general, a dynamic or semi-rigid rod is a rod that permits motion of at least one portion of the rod relative to itself. In some configurations, the dynamic rod includes two portions configured such that one portion is movable with respect to the other portion. The intersection of the two portions is typically termed a dynamic portion or dynamic joint that is located between the ends of the rod. Other configurations of dynamic or semi-rigid rods include rods having at least one reduced cross-sectional area relative to another cross-sectional area of the same rod. Other dynamic rods are dynamic as a result of the materials from which they are made such that at least one portion of the rod is flexible relative to another portion of the same rod. All types of dynamic or semi-rigid rods are within the scope of the present invention, including constructs designed to replace and/or mimic the facet. Examples of dynamic rods developed by VertiFlex, Inc. of San Clemente, Calif. are disclosed in U.S. patent application Ser. No. 11/427,738, filed Jun. 29, 2006, U.S. patent application Ser. No. 10/970,366 filed Oct. 20, 2004, U.S. patent application Ser. No. 11/006,495 filed Dec. 6, 2004, U.S. patent application Ser. No. 11/033,452 filed Jan. 10, 2005, U.S. patent application Ser. No. 11/436,407 filed on May 17, 2006, U.S. Provisional Patent Application Ser. No. 60/931,811 filed May 25, 2007, U.S. Patent Application Ser. No. 60/994,899 filed on Sep. 21, 2007, and U.S. Patent Application Ser. No. 61/063,878 filed on Feb. 6, 2008 all of which are incorporated by reference herein in their entireties for all purposes.

Figure 23:
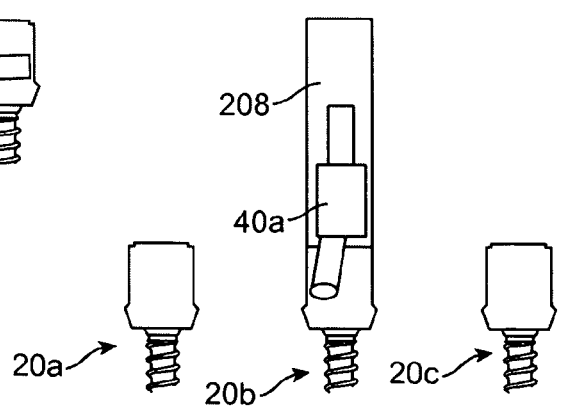
FIG. 23 illustrates three screw systems and a pivoting rod and delivery cannula connected to one of the screw systems according to the present invention.

Turning now to FIG. 22, various combinations of rods in a multi-level application of the type shown in FIG. 21 are within the scope of the present invention. Of course, various combinations employing any type of dynamic (semi-rigid), curved, bent, straight or otherwise different type of dynamic or non-dynamic rod are within the scope of the invention and employable along one and the other side of the patient's spine in the same installation. For example, FIG. 22 illustrates a typical installation of two rods 40*a* and 40*b* and bone screw systems 20*a*, 20*b*, 20*c* along one side of a patient's spine in a multi-level application joining together three vertebrae (not shown). The other side of the patient's spine is not shown however it is clear that any combination is also possible on the other side and in one variation the installation on the other side is the same. In FIG. 22A, systems 20*a*, 20*b* and 20*c* are implanted along one side of a patient's spine into three adjacent vertebrae (not shown) wherein rods 40*a*, 40*b* are both straight. In FIG. 22B, rod 40*a* is straight and rod 40*b* is a first type or second type of dynamic rod. In FIG. 22C, rod 40*a* is a first type of dynamic rod and rod 40*b* is also a first type of dynamic rod. In FIG. 22D, rod 20*a* is a first type or second type of dynamic rod. In FIG. 22E, rod 40*a* is a second type of dynamic rod and rod 40*b* is a first type of dynamic rod that is different from the second type. In FIG. 22F, both rods 40*a* and 40*b* are the same type and shown as each being a second type of dynamic rod. In FIG. 22G, rod 40*a* is a first type of dynamic rod and rod 40*b* is a second type of dynamic rod. FIG. 22 illustrates some of the possible combinations within the scope of the present invention. It should be noted that any one of the rods in FIG. 22 may also be curved. Furthermore, the arrangements shown are for configurations in which system 20*a* is placed caudal with respect to system 20*c* and configurations in which system 20*a* is implanted cephalad with respect to system 20*c*. Of course, the dynamic rod configurations are such that they are insertable and implantable through a cannulated tower 208 as shown in FIG. 23 as are the curved and non-dynamic rods.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

We claim:

1. A spinal alignment system for interconnecting vertebral bodies, comprising:
   a bone fastener;
   a seat connected to the bone fastener; said seat having a first rod receiving portion, a second rod receiving portion, a first rod channel and a second rod channel;
   a first rod configured to connect to the seat; and
   a second rod configured to connect to the seat;
   wherein the seat is configured to connect to one end of the first rod at the first rod receiving portion and independently to one end of the second rod at the second rod receiving portion such that the first rod is movable into a position projecting through the first rod channel and the second rod is movable into a position projecting through the second rod channel, wherein at least one of the first and second rods is polyaxially movable with respect to the seat while in a position projecting through a respective rod channel, wherein the seat is configured to connect to one end of the first rod at the first rod receiving portion such that a second end of the first rod is pivotable about the one end of the first rod connected to the first rod receiving portion from a first position to at least a second position, substantially perpendicular to the first position, projecting through the first rod channel, and wherein when the seat is connected to the one end of the first rod the first rod is inhibited from removal from the seat in any position from the first position to the second position;
   wherein the seat includes a top opening and the system further includes a closure mechanism adapted to be inserted into the top opening to lock the polyaxial motion of the at least one of the first and second rods.

2. The system of claim 1 wherein the bone fastener is a bone screw that is polyaxially movable with respect to the seat; and wherein the closure mechanism is adapted to be inserted into the top opening to lock the polyaxial motion of the at least one of the first and second rods simultaneously or independently with locking the polyaxial motion of the bone screw with respect to the seat.

3. The system of claim 2 wherein the seat includes:
   a coupler connected to the bone screw and to the seat.

4. The system of claim 3 wherein the coupler includes the first and second rod receiving portions.

5. The system of claim 4 wherein the retaining ring includes the first and second rod receiving portions.

6. The system of claim 3 wherein the seat includes:
   a retaining ring configured to be disposed between the seat and the coupler.

7. The system of claim 1, wherein the seat is configured to connect to one end of the second rod at the second rod receiving portion such that a second end of the second rod is pivotable about the one end of the second rod connected to the second rod receiving portion during use.

8. The system of claim 1, wherein the seat is configured to connect to one end of the second rod at the second rod receiving portion such that a second end of the second rod is pivotable about the one end of the second rod connected to the second rod receiving portion from a third position substantially in alignment with a longitudinal axis of the bone fastener to a fourth position, substantially perpendicular to the third position, projecting through the second rod channel.

9. A spinal alignment system for interconnecting vertebral bodies, comprising:
   a first bone fastener configured for spinal engagement into a first vertebra;
   a first seat connected to the first bone fastener; said first seat having at least a first rod channel and a first top opening;
   a second bone fastener configured for spinal engagement into a second vertebra;
   a second seat connected to the second bone fastener; said second seat having a first rod receiving portion and a second rod receiving portion, a second rod channel and a third rod channel and a second top opening;
   a third bone fastener configured for spinal engagement into a third vertebra;
   a third seat connected to the third bone fastener; said third seat having at least a fourth rod channel and a third top opening;
   a first rod having a first end and a second end; the first end configured to connect to the first rod receiving portion of the second seat;
   a second rod having a first end and a second end; the first end configured to connect to the second rod receiving portion of the second seat;
   wherein the second seat is configured to connect to the first end of the first rod at the first rod receiving portion and to the first end of the second rod at the second rod receiving portion such that the first rod is movable into a position, substantially perpendicular to the first rod's initial position, projecting through the second rod channel into the first rod channel and the second rod is movable into a position, substantially perpendicular to the second rod's initial position, projecting through the third rod channel into the fourth rod channel, wherein when the second seat is connected to the first end of the first rod the first rod is inhibited from removal from the second seat in any position from the initial position to the position projecting through the second rod channel, and wherein when the second seat is connected to the first end of the second rod the second rod is inhibited from removal from the second seat in any position from the initial position to the position projecting through the third rod channel;
   wherein at least one of the first and second rods is polyaxially movable with respect to the second seat while in a position projecting through a respective rod channel;
   a first closure mechanism configured to close the first top opening to secure the first rod in the first seat;
   a second closure mechanism configured to close the second top opening and lock the polyaxial motion of the at least one of the polyaxially movable first and second rods in a position within the range of polyaxial motion; and
   a third closure mechanism configured to close the third top opening to secure the second rod in the third seat.

10. The system of claim 9 wherein at least one of the first, second and third bone fastener is a bone screw.

11. The system of claim 10 wherein the at least one bone screw is polyaxially movable relative to its respective seat.

12. The system of claim 9 wherein at least one of the first and second rods is a dynamic rod, and wherein the dynamic rod comprises a first portion and a second portion such that at least the first portion is movable with respect to the second portion.

13. The system of claim 9 wherein both of the first and second rods are dynamic rods.

14. The system of claim 13 wherein the first dynamic rod is different from the second dynamic rod.

15. The system of claim 9 wherein the second closure mechanism includes a set screw and the system is configured such that advancement of set screw locks the polyaxial motion.

16. The system of claim 9 wherein at least two of the first, second and third vertebrae are adjacent vertebrae.

17. A spinal alignment system for interconnecting vertebral bodies, comprising:
- a bone fastener;
- a seat connected to the bone fastener; said seat having a first rod receiving portion, a second rod receiving portion, a first rod channel and a second rod channel;
- a first rod configured to connect to the seat; and
- a second rod configured to connect to the seat;
- wherein the seat is configured to connect to one end of the first rod at the first rod receiving portion and independently to one end of the second rod at the second rod receiving portion such that the first rod is movable into a position projecting through the first rod channel and the second rod is movable into a position projecting through the second rod channel, wherein at least one of the first and second rods is polyaxially movable with respect to the seat while in a position projecting through a respective rod channel, wherein the seat is configured to connect to one end of the first rod at the first rod receiving portion such that a second end of the first rod is pivotable about the one end of the first rod connected to the first rod receiving portion from a first position to at least a second position, substantially perpendicular to the first position, projecting through the first rod channel, and wherein when the seat is connected to the one end of the first rod the first rod is inhibited from removal from the seat in any position from the first position to the second position; and
- wherein the seat is configured to connect to one end of the second rod at the second rod receiving portion such that a second end of the second rod is pivotable about the one end of the second rod connected to the second rod receiving portion from a third position substantially in alignment with a longitudinal axis of the bone fastener to a fourth position, substantially perpendicular to the third position, projecting through the second rod channel.

18. The system of claim 17, wherein the bone fastener is a bone screw that is polyaxially movable with respect to the seat; and wherein the seat includes a top opening and the system further includes a closure mechanism adapted to be inserted into the top opening to lock the polyaxial motion of the at least one of the first and second rods simultaneously or independently with locking the polyaxial motion of the bone screw with respect to the seat.

19. The system of claim 18, wherein the seat includes:
- a coupler connected to the bone screw and to the seat.

20. The system of claim 19, wherein the coupler includes the first and second rod receiving portions.

21. The system of claim 20, wherein the retaining ring includes the first and second rod receiving portions.

22. The system of claim 19, wherein the seat includes:
- a retaining ring configured to be disposed between the seat and the coupler.

* * * * *